(12) United States Patent
Sonnewald et al.

(10) Patent No.: US 7,319,013 B2
(45) Date of Patent: Jan. 15, 2008

(54) SERINE HYDROXYMETHYLTRANSFERASE AS A TARGET FOR HERBICIDES

(75) Inventors: Uwe Sonnewald, Quedlinburg (DE); Frederik Börnke, Quedlinburg (DE); Kirsten Deist, Westdorf (DE); Marc Stitt Nigel, Potsdam (DE); Wolfgang Lein, Potsdam (DE); Thomas Ehrhardt, Speyer (DE); Andreas Reindl, Mannheim (DE); Ralf-Michael Schmidt, Kirrweiler (DE); Annette Freund, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 270 days.

(21) Appl. No.: 10/507,989

(22) PCT Filed: Mar. 13, 2003

(86) PCT No.: PCT/EP03/02574

§ 371 (c)(1),
(2), (4) Date: Sep. 16, 2004

(87) PCT Pub. No.: WO03/078613

PCT Pub. Date: Sep. 25, 2003

(65) Prior Publication Data

US 2005/0142553 A1 Jun. 30, 2005

(30) Foreign Application Priority Data

Mar. 20, 2002 (DE) .............................. 102 12 469

(51) Int. Cl.
*C12Q 1/48* (2006.01)
*C12N 9/10* (2006.01)
*C12N 5/04* (2006.01)
*C12N 5/14* (2006.01)
*C07H 21/04* (2006.01)

(52) U.S. Cl. ..................... 435/15; 435/193; 435/410; 536/23.2

(58) Field of Classification Search ............... None
See application file for complete search history.

(56) References Cited

U.S. PATENT DOCUMENTS 5,187,071 A 2/1993 Fischer et al.
6,436,657 B1 8/2002 Famodu et al.

FOREIGN PATENT DOCUMENTS

| EP | 1 033 405 A2 | 9/2000 |
|---|---|---|
| WO | WO 98/33925 | 8/1998 |
| WO | WO 00/04163 | 1/2000 |
| WO | WO 00/77185 A2 | 12/2000 |
| WO | WO 01/79514 A2 | 10/2001 |

OTHER PUBLICATIONS

The Arabidopsis Genome Initiative, Nature, 2000, 408 (6814) : 796-815.
Bouche et al, Curr. Op. Plant Biol. 4, 2001, pp. 111-117.
Kopriva S., Bauwe H.; "Serine hydroxymethyltransferase from *Solanum tuberosum*", Plant Physiology, vol. 107, No. 1, 1995, p. 271-272.
Copriva S. & Bauwe H.: Clonino and sequencing of two isoforms of serine hydroxymethyltransferase from *Flaveria pringlei*, Plant Phvsioloqv, vol. 116, 1998, p. 1603.
GenBank, Database, Jul. 17, 1997, Macas J. et al.: "0521-2 NEST Tobacco leaf 01 *Nicotiana tabacum* cDNA 3, mRNA sequence", Database accession No. AA523562.
Martin F P-D et al.: "A hybrid-potential free-energy study of the isomerization Step of the acetohydroxy acid isomeroreductase reaction", Journal of the American chemical society, Aug. 16, 2000, vol. 122, No. 32, p. 7688-7697.
Hanson Andrew D. et al.: "Plant one-carbon metabolism and its engineering", Trends in Plant Science, vol. 5, No. 5, (May 2000), p. 206-213.
Douce Roland et al.: "The glycine decarboxylase system": A fascinating complex, Trends in Plant Science, vol. 6, No. 4, (Apr. 2001), p. 167-176.
P. J. Lea et al.: "The use of mutants and transgenic plants to study amino acid metabolism", Plant Cell and environment, vol. 17, No. 5,1994,p. 541-556.
Ashworth D J et al.: "Direct observation of Glycine metabolism in Tobacco Nicotiana-Tabacum suspension cells by carbon-13, NMR SPECTROSCOPY", Biochemistry, vol. 23, No. 10, 1984,p. 2252-2257.
Peterson R B: "Regulation of Glycine Decarboxylase and L Serine Hydroxymethyl Transferase Activities by Glyoxylate in Tobacco NicotianaTabacum Cultivar, John-Williams-Broadleaf Leaf Mitochondrial, Preparations", Plant Physiology (Bethesda), vol. 70, No. 1, 1982,p. 61-66.
Database GENSEQ, Alexandrov N. et al.: "*Arabidopsis thaliana* protein fragment" SEQ ID No. 54248, XP002250359, Database accession No. AAG43405, Oct. 18, 2000.

(Continued)

*Primary Examiner*—Elizabeth Slobodyansky
(74) *Attorney, Agent, or Firm*—Rothwell, Figg, Ernst & Manbeck, P.C.

(57) ABSTRACT

The present invention relates to serine hydroxymethyltransferase (E.C. 2.1.2.1) as novel target for herbicides, and to nucleic acid sequences encoding a polypeptide with the biological activity of a serine hydroxymethyltransferase, which, when not present, bring about growth retardation symptoms and chlorotic leaves, comprising the nucleic acid sequence SEQ ID No:3, and functional equivalents of the abovementioned nucleic acid sequence or the nucleic acid sequence SEQ ID NO:7 and functional equivalents of the abovementioned nucleic acid sequence. Moreover, the present invention relates to the use of the abovementioned nucleic acid sequences, of functional analogs of the SEQ ID NO:3 or SEQ ID NO:7 or of polypeptides encoded by one of the abovementioned nucleic acid sequences in a method for identifying herbicidally active compounds which inhibit serine hydroxymethyltransferases, and to the use of these compounds which have been identified by the method as herbicides.

8 Claims, No Drawings

OTHER PUBLICATIONS

Database GENSEQ, Alexandrov N. et al.: "*Arabidopsis thaliana* protein fragment"SEQ ID No. 54249, XP 002250360, Database accession No. AAG43406, Oct. 18, 2000.

Database GENSEQ, Alexandrov N. et al.: "*Arabidopsis thaliana* protein fragment"SEQ ID No. 54250, XP 002250361, Database accession No. AAG43407, Oct. 18, 2000.

Database GENSEQ, Alexandrov N. et al.: Zea mays protein fragment SEQ ID No. 41407, XP 002250362 Database accession No. AAG34075, Oct. 18, 2000.

Database GENSEQ, Alexandrov N. et al.: Zea mays protein fragment SEQ ID No. 41406, XP 002250363Database accession No. AAG34074, Oct. 18, 2000.

Database GENSEQ, Alexandrov N. et al.: Zea mays protein fragment SEQ ID No. 41408, XP 002250364Database accession No. AAG34076, Oct. 18, 2000.

Database EMBL, Turner S. R. et al.: Pisum sativum serine hydroxymethyltransferase mRNA, complete cds, Database accession No. M87649, Aug. 29, 1992.

Database EMBL, Bauwe H.: "*Flaveria pringlei* mRNA for glicine hydroxymethyltransferase", database accession No. 225860.

Database EMBL, Database, Nov. 20, 2001, Wang H. & Bohnert H.: ,Zea mays serine hydroxymethyltransferase mRNA, partial cds, Database accession No. AF439728.

SEQUENCE LISTING

<160> NUMBER OF SEQ ID NOS: 29

<210> SEQ ID NO 1
<211> LENGTH: 884
<212> TYPE: DNA
<213> ORGANISM: Nicotiana tabacum
<220> FEATURE:
<221> NAME/KEY: CDS
<222> LOCATION: (506)..(652)

<400> SEQUENCE: 1
gcggccgctc tcaagcgttg catgactgta catgtacaca ggtggcattg ctctcaggca      60

-continued

```
aatgccaaga agttggagtc gaagatactg catgaccttg caattagaac agttccaaac      120
ccaaattggt cagcctgcag catctggcat gtctatcttg ggtcaacgag ccaaactcaa      180
gaataaaatt ggctgggaaa accttctgat ggtttactgt agatatattc acttcctatg      240
caaacattgc cctaggcctg agaagtgaca gacagactag caggaccgct tgtcagggcc      300
tttcagactt ggagctgcgc gcttgttcat ggtagatata catggacatt tgtcaaacac      360
agcatgacat cactttactt gctagcattt ccatcttctc tagcaaagca cagaagtcgg      420
atggagccat ctgacacccc ctgcagacag ccacctttg gcaggctgca ctggcgcatg       480
ccagcagaaa ctgctagcgg ccgct gga aca aag ttg aaa gac ttt gtg aca        532
                            Gly Thr Lys Leu Lys Asp Phe Val Thr
                             1               5 aca cta cag tct agc gct tca atc cag tcg gag att gca aaa ctc cgc        580
Thr Leu Gln Ser Ser Ala Ser Ile Gln Ser Glu Ile Ala Lys Leu Arg
 10              15                  20                  25 cat ggt gtg gag gag tat gca aag cag ttc cct aca att gga ttt gag        628
His Gly Val Glu Glu Tyr Ala Lys Gln Phe Pro Thr Ile Gly Phe Glu
             30                  35                  40 aag gaa acc atg aag tac aaa aac tgagagctcg actgagtata tacacaaggg       682
Lys Glu Thr Met Lys Tyr Lys Asn
                 45 accaatatcc aacatcctca aggtgaatgg gatagacatc caaactgcag ttcgctccca      742 aggattggat tgtcatcttt tactaatact atgtaaaatc cagcagtgtt tggttcctaa      802 gtttgccact ttgtatatta acgattgtaa ttctactgag gtccttgaaa gcaataaact      862 cctgttgtct cggagcggcc gc                                               884

<210> SEQ ID NO 2
<211> LENGTH: 49
<212> TYPE: PRT
<213> ORGANISM: Nicotiana tabacum

<400> SEQUENCE: 2

Gly Thr Lys Leu Lys Asp Phe Val Thr Thr Leu Gln Ser Ser Ala Ser
 1               5                  10                  15

Ile Gln Ser Glu Ile Ala Lys Leu Arg His Gly Val Glu Glu Tyr Ala
             20                  25                  30

Lys Gln Phe Pro Thr Ile Gly Phe Glu Lys Glu Thr Met Lys Tyr Lys
         35                  40                  45

Asn

<210> SEQ ID NO 3
<211> LENGTH: 772
<212> TYPE: DNA
<213> ORGANISM: Nicotiana tabacum
<220> FEATURE:
<221> NAME/KEY: CDS
<222> LOCATION: (2)..(541)

<400> SEQUENCE: 3 g cgg ccg ctg gca gtt gct ttg aaa cag gca atg act cca gaa tac aga      49
  Arg Pro Leu Ala Val Ala Leu Lys Gln Ala Met Thr Pro Glu Tyr Arg
   1               5                  10                  15 gct tac caa gag caa tgc ctt agc aac tgc tca aaa ttt gcc cag gct        97
Ala Tyr Gln Glu Gln Cys Leu Ser Asn Cys Ser Lys Phe Ala Gln Ala
             20                  25                  30 tta gcg gga atg ggt tat gaa ctt gtt tct ggt gga aca gag aat cac        145
Leu Ala Gly Met Gly Tyr Glu Leu Val Ser Gly Gly Thr Glu Asn His
         35                  40                  45
```

```
ttg gtt ttg gtg aac ttg aaa aac aag ggt att gat ggt tct agg gtt      193
Leu Val Leu Val Asn Leu Lys Asn Lys Gly Ile Asp Gly Ser Arg Val
 50                  55                  60 gaa aaa gtt ttg gaa gcg gta cat att gca gcg aat aag aac act gtt      241
Glu Lys Val Leu Glu Ala Val His Ile Ala Ala Asn Lys Asn Thr Val
 65                  70                  75                  80 cct gga gat gta tcc gcc atg gtc cct ggt ggc atc aga atg ggg act      289
Pro Gly Asp Val Ser Ala Met Val Pro Gly Gly Ile Arg Met Gly Thr
                 85                  90                  95 cct gca ctc aca tca agg gga ttt att gag gaa gat ttt gtg aaa gtt      337
Pro Ala Leu Thr Ser Arg Gly Phe Ile Glu Glu Asp Phe Val Lys Val
            100                 105                 110 gct gaa ttc ttt gat gct gct gtg aag ata gca gtg aaa ata aag act      385
Ala Glu Phe Phe Asp Ala Ala Val Lys Ile Ala Val Lys Ile Lys Thr
            115                 120                 125 gaa gct caa gga aca aag ttg aaa gac ttt gtg aca aca cta cag tct      433
Glu Ala Gln Gly Thr Lys Leu Lys Asp Phe Val Thr Thr Leu Gln Ser
130                 135                 140 agc gct cca atc cag tcg gag att gca aaa ctc cgc cat ggt gtg gag      481
Ser Ala Pro Ile Gln Ser Glu Ile Ala Lys Leu Arg His Gly Val Glu
145                 150                 155                 160 gag tat gca aag cag ttc cct aca att ggg ttt gag aag gaa acc atg      529
Glu Tyr Ala Lys Gln Phe Pro Thr Ile Gly Phe Glu Lys Glu Thr Met
                165                 170                 175 aag tac aaa aac tgagagctcg actgagtata tacacaaggg accaatatcc          581
Lys Tyr Lys Asn
            180 aacatcctca aggtgaatgg gatagacatc caaactgcag ttcgctccca aggattggat    641 tgtcatcttt tactaatact atgtaaaatc cagcagtgtt tggttcctaa gtttgccact    701 ttgtatatta acgattgtaa ttctactgag gtccttgaaa gcaataaact cctgttgtct    761 cgagcggccg c                                                        772

<210> SEQ ID NO 4
<211> LENGTH: 180
<212> TYPE: PRT
<213> ORGANISM: Nicotiana tabacum

<400> SEQUENCE: 4

Arg Pro Leu Ala Val Ala Leu Lys Gln Ala Met Thr Pro Glu Tyr Arg
 1               5                  10                  15

Ala Tyr Gln Glu Gln Cys Leu Ser Asn Cys Ser Lys Phe Ala Gln Ala
                 20                  25                  30

Leu Ala Gly Met Gly Tyr Glu Leu Val Ser Gly Gly Thr Glu Asn His
             35                  40                  45

Leu Val Leu Val Asn Leu Lys Asn Lys Gly Ile Asp Gly Ser Arg Val
 50                  55                  60

Glu Lys Val Leu Glu Ala Val His Ile Ala Ala Asn Lys Asn Thr Val
 65                  70                  75                  80

Pro Gly Asp Val Ser Ala Met Val Pro Gly Gly Ile Arg Met Gly Thr
                 85                  90                  95

Pro Ala Leu Thr Ser Arg Gly Phe Ile Glu Glu Asp Phe Val Lys Val
            100                 105                 110

Ala Glu Phe Phe Asp Ala Ala Val Lys Ile Ala Val Lys Ile Lys Thr
            115                 120                 125

Glu Ala Gln Gly Thr Lys Leu Lys Asp Phe Val Thr Thr Leu Gln Ser
130                 135                 140
```

```
Ser Ala Pro Ile Gln Ser Glu Ile Ala Lys Leu Arg His Gly Val Glu
145                 150                 155                 160

Glu Tyr Ala Lys Gln Phe Pro Thr Ile Gly Phe Glu Lys Glu Thr Met
                165                 170                 175

Lys Tyr Lys Asn
            180

<210> SEQ ID NO 5
<211> LENGTH: 564
<212> TYPE: DNA
<213> ORGANISM: Nicotiana tabacum
<220> FEATURE:
<221> NAME/KEY: CDS
<222> LOCATION: (10)..(330)

<400> SEQUENCE: 5 gcggccgct gca gcg aat aag aac act gtt cct gga gat gta tct gcc atg      51
           Ala Ala Asn Lys Asn Thr Val Pro Gly Asp Val Ser Ala Met
             1               5                  10 gtc cct ggt ggc atc aga atg ggg act ctt gca ctc aca tca agg gga       99
Val Pro Gly Gly Ile Arg Met Gly Thr Leu Ala Leu Thr Ser Arg Gly
 15              20                  25                  30 ttt att gag gaa gat ttt gtg aaa gtt gct gaa ttc ttt gat gct gct      147
Phe Ile Glu Glu Asp Phe Val Lys Val Ala Glu Phe Phe Asp Ala Ala
                 35                  40                  45 gtg aag ata gca gtg aaa ata aag act gaa gct caa gga aca aag ttg      195
Val Lys Ile Ala Val Lys Ile Lys Thr Glu Ala Gln Gly Thr Lys Leu
     50                  55                  60 aaa gac ttt gtg aca aca cta cag tct agc gct tca atc cag tcg gag      243
Lys Asp Phe Val Thr Thr Leu Gln Ser Ser Ala Ser Ile Gln Ser Glu
 65                  70                  75 att gca aaa ctc cgc cat ggt gtg gag gag tat gca aag cag ttc cct      291
Ile Ala Lys Leu Arg His Gly Val Glu Glu Tyr Ala Lys Gln Phe Pro
             80                  85                  90 aca att ggg ttt gag aag gaa acc atg aag tac aaa aac tgagagctcg       340
Thr Ile Gly Phe Glu Lys Glu Thr Met Lys Tyr Lys Asn
 95                 100                 105 actgagtata tacacaaggg accaatatcc aacatcctca aggtgaatgg gatagacatc    400
caaactgcag ttcgctccca aggattggat tgtcatcttt tactaatact atgtaaaatc    460
cagcagtgtt tggttcccaa gtttgccact ttgtatatta acgattgtaa ttcttctgag    520
gtccttgaaa gcaataaact cctgttgtca cggtaagcgg ccgc                     564

<210> SEQ ID NO 6
<211> LENGTH: 107
<212> TYPE: PRT
<213> ORGANISM: Nicotiana tabacum

<400> SEQUENCE: 6

Ala Ala Asn Lys Asn Thr Val Pro Gly Asp Val Ser Ala Met Val Pro
  1               5                  10                  15

Gly Gly Ile Arg Met Gly Thr Leu Ala Leu Thr Ser Arg Gly Phe Ile
             20                  25                  30

Glu Glu Asp Phe Val Lys Val Ala Glu Phe Phe Asp Ala Ala Val Lys
         35                  40                  45

Ile Ala Val Lys Ile Lys Thr Glu Ala Gln Gly Thr Lys Leu Lys Asp
     50                  55                  60

Phe Val Thr Thr Leu Gln Ser Ser Ala Ser Ile Gln Ser Glu Ile Ala
 65                  70                  75                  80
```

```
Lys Leu Arg His Gly Val Glu Glu Tyr Ala Lys Gln Phe Pro Thr Ile
                85                  90                  95
Gly Phe Glu Lys Glu Thr Met Lys Tyr Lys Asn
            100                 105

<210> SEQ ID NO 7
<211> LENGTH: 1835
<212> TYPE: DNA
<213> ORGANISM: Nicotiana tabacum
<220> FEATURE:
<221> NAME/KEY: CDS
<222> LOCATION: (56)..(1609)

<400> SEQUENCE: 7
gcacccaaaa cacaagtcat ttgggtgtgt gtaacagggg gagaagctca caatt atg      58
                                                              Met
                                                              1 gcc atg gca acg gct ctt cga aga ctt tcc tct tct gtt gac aaa cca     106
Ala Met Ala Thr Ala Leu Arg Arg Leu Ser Ser Ser Val Asp Lys Pro
        5                   10                  15 att aag cgt ctc tat aat ggc ggc tct ctc tat tac atg tca tcg ttg     154
Ile Lys Arg Leu Tyr Asn Gly Gly Ser Leu Tyr Tyr Met Ser Ser Leu
    20                  25                  30 cct aat gaa gct gtt tac gag aag gaa aaa aat ggt gtc acg tgg cca     202
Pro Asn Glu Ala Val Tyr Glu Lys Glu Lys Asn Gly Val Thr Trp Pro
35                  40                  45 aag caa ctt aat gct cct cta gag gag gtt gat cca gaa att gct gac     250
Lys Gln Leu Asn Ala Pro Leu Glu Glu Val Asp Pro Glu Ile Ala Asp
50                  55                  60                  65 att att gag ctt gag aaa gca cgc cag tgg aag gga ctt gaa ctc att     298
Ile Ile Glu Leu Glu Lys Ala Arg Gln Trp Lys Gly Leu Glu Leu Ile
                70                  75                  80 cct tca gaa aat ttc act tct gtg tct gta atg caa gct gtt gga tct     346
Pro Ser Glu Asn Phe Thr Ser Val Ser Val Met Gln Ala Val Gly Ser
            85                  90                  95 gtt atg aca aac aag tac agt gaa gga tac cct ggg gct aga tac tat     394
Val Met Thr Asn Lys Tyr Ser Glu Gly Tyr Pro Gly Ala Arg Tyr Tyr
            100                 105                 110 gga gga aat gag tat att gac atg gcg gaa acc tta tgc cag aaa cgt     442
Gly Gly Asn Glu Tyr Ile Asp Met Ala Glu Thr Leu Cys Gln Lys Arg
    115                 120                 125 gct tta gaa gcc ttc agg ttg gat cct gca aaa tgg gga gtg aat gtg     490
Ala Leu Glu Ala Phe Arg Leu Asp Pro Ala Lys Trp Gly Val Asn Val
130                 135                 140                 145 cag cct ctg tca gga tca cct gct aat ttt cat gtt tac act gca ctt     538
Gln Pro Leu Ser Gly Ser Pro Ala Asn Phe His Val Tyr Thr Ala Leu
                150                 155                 160 tta aaa cct cat gaa aga atc atg gcc ctt gat ctt ccc cac ggt gga     586
Leu Lys Pro His Glu Arg Ile Met Ala Leu Asp Leu Pro His Gly Gly
            165                 170                 175 cat ctt tct cat gga tat cag act gat aca aag aag ata tct gcc gtc     634
His Leu Ser His Gly Tyr Gln Thr Asp Thr Lys Lys Ile Ser Ala Val
            180                 185                 190 tct ata ttt ttt gag acc atg cca tat aga ctg aat gag agc act ggc     682
Ser Ile Phe Phe Glu Thr Met Pro Tyr Arg Leu Asn Glu Ser Thr Gly
    195                 200                 205 tac att gac tat gac cag ctt gag aaa agt gcc aca ctc ttt agg cca     730
Tyr Ile Asp Tyr Asp Gln Leu Glu Lys Ser Ala Thr Leu Phe Arg Pro
210                 215                 220                 225 aag tta att gtc gct ggt gct agt gct tat gca cgt ctt tat gac tat     778
```

```
                                      -continued

Lys Leu Ile Val Ala Gly Ala Ser Ala Tyr Ala Arg Leu Tyr Asp Tyr
                230                 235                 240 gca cgt atc cga aag gtt tgt gac aaa cag aag gct atc atg ttg gca      826
Ala Arg Ile Arg Lys Val Cys Asp Lys Gln Lys Ala Ile Met Leu Ala
            245                 250                 255 gat atg gct cat att agt ggg tta gtt gca gct gga gtc atc cca tca      874
Asp Met Ala His Ile Ser Gly Leu Val Ala Ala Gly Val Ile Pro Ser
        260                 265                 270 cca ttt gat tat gca gat gtt gtg acc acc aca acc cac aaa tcc ctt      922
Pro Phe Asp Tyr Ala Asp Val Val Thr Thr Thr Thr His Lys Ser Leu
    275                 280                 285 cgc ggg cct cgt ggt gcc atg att ttc ttc cgg aag ggt gtg aag gag      970
Arg Gly Pro Arg Gly Ala Met Ile Phe Phe Arg Lys Gly Val Lys Glu
290                 295                 300                 305 gtt aac aag caa ggc aag gag gtg ttg tac gac tat gaa gat aaa att     1018
Val Asn Lys Gln Gly Lys Glu Val Leu Tyr Asp Tyr Glu Asp Lys Ile
                310                 315                 320 aac cag gca gtc ttt ccc gga ctt caa ggt ggt cct cac aac cat aca     1066
Asn Gln Ala Val Phe Pro Gly Leu Gln Gly Gly Pro His Asn His Thr
            325                 330                 335 att act ggc ttg gca gtt gct ttg aaa cag gca atg act cca gaa tac     1114
Ile Thr Gly Leu Ala Val Ala Leu Lys Gln Ala Met Thr Pro Glu Tyr
        340                 345                 350 aga gct tac caa gag caa tgc ctt agc aac tgc tca aaa ttt gcc cag     1162
Arg Ala Tyr Gln Glu Gln Cys Leu Ser Asn Cys Ser Lys Phe Ala Gln
    355                 360                 365 gct tta gcg gga atg ggt tat gaa ctt gtt tct ggt gga aca gag aat     1210
Ala Leu Ala Gly Met Gly Tyr Glu Leu Val Ser Gly Gly Thr Glu Asn
370                 375                 380                 385 cac ttg gtt ttg gtg aac ttg aaa aac aag ggt att gat ggt tct agg     1258
His Leu Val Leu Val Asn Leu Lys Asn Lys Gly Ile Asp Gly Ser Arg
                390                 395                 400 gtt gaa aaa gtt ttg gaa gcg gta cat att gca gcg aat aag aac act     1306
Val Glu Lys Val Leu Glu Ala Val His Ile Ala Ala Asn Lys Asn Thr
            405                 410                 415 gtt cct gga gat gta tct gcc atg gtc cct ggt ggc atc aga atg ggg     1354
Val Pro Gly Asp Val Ser Ala Met Val Pro Gly Gly Ile Arg Met Gly
        420                 425                 430 act cct gca ctc aca tca agg gga ttt att gag gaa gat ttt gtg aaa     1402
Thr Pro Ala Leu Thr Ser Arg Gly Phe Ile Glu Glu Asp Phe Val Lys
    435                 440                 445 gtt gct gaa ttc ttt gat gct gct gtg aag ata gca gtg aaa ata aag     1450
Val Ala Glu Phe Phe Asp Ala Ala Val Lys Ile Ala Val Lys Ile Lys
450                 455                 460                 465 act gaa gct caa gga aca aag ttg aaa gac ttt gtg aca aca cta cag     1498
Thr Glu Ala Gln Gly Thr Lys Leu Lys Asp Phe Val Thr Thr Leu Gln
                470                 475                 480 tct agc gct tca atc cag tcg gag att gca aaa ctc cgc cat ggt gtg     1546
Ser Ser Ala Ser Ile Gln Ser Glu Ile Ala Lys Leu Arg His Gly Val
            485                 490                 495 gag gag tat gca aag cag ttc cct aca att ggg ttt gag aag gaa acc     1594
Glu Glu Tyr Ala Lys Gln Phe Pro Thr Ile Gly Phe Glu Lys Glu Thr
        500                 505                 510 atg aag tac aaa aac tgagagctcg actgagtata tacacaaggg accaatatcc    1649
Met Lys Tyr Lys Asn
        515 aacatcctca aggtgaatgg gatagacatc caaactgcag ttcgctccca aggattggat   1709 tgtcatcttt tactaatact atgtaaaatc cagcagtgtt tggttcccaa gtttgccact   1769
```

```
ttgtatatta acgattgtaa ttcttctgag gtccttgaaa gcaataaact cctgttgtca    1829
cggtaa                                                               1835
```

<210> SEQ ID NO 8
<211> LENGTH: 518
<212> TYPE: PRT
<213> ORGANISM: Nicotiana tabacum

<400> SEQUENCE: 8

```
Met Ala Met Ala Thr Ala Leu Arg Arg Leu Ser Ser Val Asp Lys
1               5                   10                  15

Pro Ile Lys Arg Leu Tyr Asn Gly Gly Ser Leu Tyr Tyr Met Ser Ser
                20                  25                  30

Leu Pro Asn Glu Ala Val Tyr Glu Lys Glu Lys Asn Gly Val Thr Trp
            35                  40                  45

Pro Lys Gln Leu Asn Ala Pro Leu Glu Glu Val Asp Pro Glu Ile Ala
    50                  55                  60

Asp Ile Ile Glu Leu Glu Lys Ala Arg Gln Trp Lys Gly Leu Glu Leu
65                  70                  75                  80

Ile Pro Ser Glu Asn Phe Thr Ser Val Ser Val Met Gln Ala Val Gly
                85                  90                  95

Ser Val Met Thr Asn Lys Tyr Ser Glu Gly Tyr Pro Gly Ala Arg Tyr
                100                 105                 110

Tyr Gly Gly Asn Glu Tyr Ile Asp Met Ala Glu Thr Leu Cys Gln Lys
            115                 120                 125

Arg Ala Leu Glu Ala Phe Arg Leu Asp Pro Ala Lys Trp Gly Val Asn
    130                 135                 140

Val Gln Pro Leu Ser Gly Ser Pro Ala Asn Phe His Val Tyr Thr Ala
145                 150                 155                 160

Leu Leu Lys Pro His Glu Arg Ile Met Ala Leu Asp Leu Pro His Gly
                165                 170                 175

Gly His Leu Ser His Gly Tyr Gln Thr Asp Thr Lys Lys Ile Ser Ala
            180                 185                 190

Val Ser Ile Phe Phe Glu Thr Met Pro Tyr Arg Leu Asn Glu Ser Thr
    195                 200                 205

Gly Tyr Ile Asp Tyr Asp Gln Leu Glu Lys Ser Ala Thr Leu Phe Arg
210                 215                 220

Pro Lys Leu Ile Val Ala Gly Ala Ser Ala Tyr Ala Arg Leu Tyr Asp
225                 230                 235                 240

Tyr Ala Arg Ile Arg Lys Val Cys Asp Lys Gln Lys Ala Ile Met Leu
                245                 250                 255

Ala Asp Met Ala His Ile Ser Gly Leu Val Ala Ala Gly Val Ile Pro
            260                 265                 270

Ser Pro Phe Asp Tyr Ala Asp Val Val Thr Thr Thr His Lys Ser
    275                 280                 285

Leu Arg Gly Pro Arg Gly Ala Met Ile Phe Phe Arg Lys Gly Val Lys
    290                 295                 300

Glu Val Asn Lys Gln Gly Lys Glu Val Leu Tyr Asp Tyr Glu Asp Lys
305                 310                 315                 320

Ile Asn Gln Ala Val Phe Pro Gly Leu Gln Gly Gly Pro His Asn His
                325                 330                 335

Thr Ile Thr Gly Leu Ala Val Ala Leu Lys Gln Ala Met Thr Pro Glu
            340                 345                 350

Tyr Arg Ala Tyr Gln Glu Gln Cys Leu Ser Asn Cys Ser Lys Phe Ala
```

```
            355                 360                 365
Gln Ala Leu Ala Gly Met Gly Tyr Glu Leu Val Ser Gly Gly Thr Glu
    370                 375                 380

Asn His Leu Val Leu Val Asn Leu Lys Asn Lys Gly Ile Asp Gly Ser
385                 390                 395                 400

Arg Val Glu Lys Val Leu Glu Ala Val His Ile Ala Ala Asn Lys Asn
                405                 410                 415

Thr Val Pro Gly Asp Val Ser Ala Met Val Pro Gly Gly Ile Arg Met
            420                 425                 430

Gly Thr Pro Ala Leu Thr Ser Arg Gly Phe Ile Glu Glu Asp Phe Val
            435                 440                 445

Lys Val Ala Glu Phe Phe Asp Ala Ala Val Lys Ile Ala Val Lys Ile
450                 455                 460

Lys Thr Glu Ala Gln Gly Thr Lys Leu Lys Asp Phe Val Thr Thr Leu
465                 470                 475                 480

Gln Ser Ser Ala Ser Ile Gln Ser Glu Ile Ala Lys Leu Arg His Gly
                485                 490                 495

Val Glu Glu Tyr Ala Lys Gln Phe Pro Thr Ile Gly Phe Glu Lys Glu
            500                 505                 510

Thr Met Lys Tyr Lys Asn
        515

<210> SEQ ID NO 9
<211> LENGTH: 16
<212> TYPE: DNA
<213> ORGANISM: Nicotiana tabacum

<400> SEQUENCE: 9
agaattcgcg gccgct                                                       16

<210> SEQ ID NO 10
<211> LENGTH: 32
<212> TYPE: DNA
<213> ORGANISM: Artificial Sequence
<220> FEATURE:
<223> OTHER INFORMATION: oligonucleotide primer with homology to
      pUC18SbfI vector

<400> SEQUENCE: 10
ctcatgcggc cgcgcgcaac gcaattaatg tg                                     32

<210> SEQ ID NO 11
<211> LENGTH: 32
<212> TYPE: DNA
<213> ORGANISM: Artificial Sequence
<220> FEATURE:
<223> OTHER INFORMATION: oligonucleotide primer with homology to
      pUC18SbfI vector

<400> SEQUENCE: 11
tcatgcggcc gcgagatcca gttcgatgta ac                                     32

<210> SEQ ID NO 12
<211> LENGTH: 21
<212> TYPE: DNA
<213> ORGANISM: Nicotiana tabacum

<400> SEQUENCE: 12
gtggattgat gtgatatctc c                                                 21
```

```
<210> SEQ ID NO 13
<211> LENGTH: 21
<212> TYPE: DNA
<213> ORGANISM: Nicotiana tabacum

<400> SEQUENCE: 13
gtaaggatct gagctacaca t                                          21

<210> SEQ ID NO 14
<211> LENGTH: 19
<212> TYPE: DNA
<213> ORGANISM: Arabidopsis thaliana

<400> SEQUENCE: 14
aaatggcgat ggccatggc                                             19

<210> SEQ ID NO 15
<211> LENGTH: 21
<212> TYPE: DNA
<213> ORGANISM: Arabidopsis thaliana

<400> SEQUENCE: 15
tggggtgaaa cagtttagtt c                                          21

<210> SEQ ID NO 16
<211> LENGTH: 20
<212> TYPE: DNA
<213> ORGANISM: Arabidopsis thaliana

<400> SEQUENCE: 16
aaaccagaga tagagagagg                                            20

<210> SEQ ID NO 17
<211> LENGTH: 22
<212> TYPE: DNA
<213> ORGANISM: Arabidopsis thaliana

<400> SEQUENCE: 17
acatgtatca tctatacatt cc                                         22

<210> SEQ ID NO 18
<211> LENGTH: 18
<212> TYPE: DNA
<213> ORGANISM: Arabidopsis thaliana

<400> SEQUENCE: 18
atggcgatgg ccatggct                                              18

<210> SEQ ID NO 19
<211> LENGTH: 21
<212> TYPE: DNA
<213> ORGANISM: Arabidopsis thaliana

<400> SEQUENCE: 19
tggggtgaaa cagtttagtt c                                          21

<210> SEQ ID NO 20
<211> LENGTH: 21
<212> TYPE: DNA
<213> ORGANISM: Arabidopsis thaliana

<400> SEQUENCE: 20
atgaaggaaa gatctcgtgt c                                          21
```

-continued

```
<210> SEQ ID NO 21
<211> LENGTH: 21
<212> TYPE: DNA
<213> ORGANISM: Arabidopsis thaliana

<400> SEQUENCE: 21
tggggtgaaa cagtttagtt c                                              21

<210> SEQ ID NO 22
<211> LENGTH: 19
<212> TYPE: DNA
<213> ORGANISM: Arabidopsis thaliana

<400> SEQUENCE: 22
atgtctttgc ccagtgaag                                                 19

<210> SEQ ID NO 23
<211> LENGTH: 21
<212> TYPE: DNA
<213> ORGANISM: Arabidopsis thaliana

<400> SEQUENCE: 23
tggggtgaaa cagtttagtt c                                              21

<210> SEQ ID NO 24
<211> LENGTH: 21
<212> TYPE: DNA
<213> ORGANISM: Arabidopsis thaliana

<400> SEQUENCE: 24
atgaaggaaa gatctcgtgt c                                              21

<210> SEQ ID NO 25
<211> LENGTH: 21
<212> TYPE: DNA
<213> ORGANISM: Arabidopsis thaliana

<400> SEQUENCE: 25
tggggtgaaa cagtttagtt c                                              21

<210> SEQ ID NO 26
<211> LENGTH: 18
<212> TYPE: DNA
<213> ORGANISM: Arabidopsis thaliana

<400> SEQUENCE: 26
atggcgatgg ccatggct                                                  18

<210> SEQ ID NO 27
<211> LENGTH: 21
<212> TYPE: DNA
<213> ORGANISM: Arabidopsis thaliana

<400> SEQUENCE: 27
tggggtgaaa cagtttagtt c                                              21

<210> SEQ ID NO 28
<211> LENGTH: 25
<212> TYPE: DNA
<213> ORGANISM: Artificial Sequence
<220> FEATURE:
<223> OTHER INFORMATION: oligonucleotide primer with homology to
      pCR 2.1 TOPO vector with NAD-dependent
      methylenetetrahydrofolate dehyrdrogenase (MTD) insert
```

```
<400> SEQUENCE: 28
tttttcttta gacagttcta cgttc                                              25

<210> SEQ ID NO 29
<211> LENGTH: 19
<212> TYPE: DNA
<213> ORGANISM: Artificial Sequence
<220> FEATURE:
<223> OTHER INFORMATION: oligonucleotide primer with homology to pCR
      2.1 TOPO vector with NAD-dependent  methylenetetrahydrofolate
      dehyrdrogenase (MTD) insert

<400> SEQUENCE: 29
atgtcgaagc ctggtcgta                                                     19
```

SERINE HYDROXYMETHYLTRANSFERASE AS A TARGET FOR HERBICIDES

CROSS REFERENCE TO RELATED APPLICATION

This application is a 35 USC §371 National Phase Entry Application from PCT/EP03/02574, filed Mar. 13, 2003, and designating the U.S.

Material inserted is indicated by underlining.

The present invention relates to serine hydroxymethyltransferase (E.C. 2.1.2.1) as novel target for herbicides, and to nucleic acid sequences encoding a polypeptide with the biological activity of a serine hydroxymethyltransferase, which, when not present, bring about growth retardation symptoms and karotic leaves, comprising the nucleic acid sequence SEQ ID No:3, and functional equivalents of the abovementioned nucleic acid sequence, or the nucleic acid sequence SEQ ID NO:7 and functional equivalents of the abovementioned nucleic acid sequence. Moreover, the present invention relates to the use of the abovementioned nucleic acid sequences, of functional analogs of the SEQ ID NO:3 or SEQ ID NO:7 or of polypeptides encoded by one of the abovementioned nucleic acid sequences in a method for identifying herbicidally active compounds which inhibit serine hydroxymethyltransferases, and to the use of these compounds which have been identified by the method as herbicides.

The basic principle of identifying herbicides via inhibiting a defined target is known (for example U.S. Pat. No. 5,187,071, WO 98/33925, WO 00/77185). In general, there is a great demand for the detection of enzymes which might constitute novel targets for herbicides. Reasons hereof are that herbicidal active ingredients which act on known targets show the development of resistance problems, and the constant endeavor to identify novel herbicidal active ingredients which are distinguished by as broad as possible a range of action, eco friendliness and toxicological compatibility and/or low application rates.

In practice, the detection of novel targets always entails great difficulties since the inhibition of an enzyme which is part of a metabolic pathway frequency has no further effect on the plant's growth. The reason may be that the plant switches over to alternative metabolic pathways whose existence is not known, or that the enzyme which is being inhibited is not limiting for the metabolic pathway. Furthermore, plant genomes are distinguished by a high degree of functional redundance. In the *Arabidopsis thaliana* genome, functionally equivalent enzymes are more frequently found in gene families than is the case with insects or mammals (Nature, 2000, 408(6814): 796-815). This hypothesis is confirmed experimentally by the fact that large gene knockout programs by the insertion of T-DNA or transposons into *Arabidopsis* have, as yet, yielded fewer manifested phenotypes than expected (Curr. Op. Plant Biol. 4, 2001, pp. 111-117).

It is an object of the present invention to identify novel targets which are essential for the growth of plants or whose inhibition lead to reduced plant growth, and to provide methods which are suitable for identifying herbicidally active compounds.

We have found that this object is achieved by the provision of serine hydroxymethyltransferase (SHMT) as novel target for herbicides and by the provision of nucleic acid sequences encoding polypeptide with the biological activity of an SHMT comprising a) a nucleic acid sequence with the nucleic acid sequence shown in SEQ ID NO:3; or
b) a nucleic acid sequence which, on the basis of the degeneracy of the genetic code, can be derived from the amino acid sequence shown in SEQ ID NO:4 by back translation; or
c) functional equivalents of the nucleic acid sequence SEQ ID NO:3 comprising a part-region with at least 91% identity to the SEQ ID NO:3;

and of nucleic acid sequences comprising
a) a nucleic acid sequence with the nucleic acid sequence shown in SEQ ID NO:7; or
b) a nucleic acid sequence which, on the basis of the degeneracy of the genetic code, can be derived from the amino acid sequence shown in SEQ ID NO:8 by back translation; or
c) functional equivalents of the nucleic acid sequence SEQ ID NO:7 with at least 88% identity to the SEQ ID NO:7.

The term "comprising" or "to comprise", when referring to nucleic acid or amino acid sequences, is understood as meaning that the nucleic acid sequence according to the invention may comprise, at the 3' or at the 5' end, additional nucleic acid sequences, where the length of the additional nucleic acid sequences does not exceed 2000 bp at the 5' and 3' end of the nucleic acid sequences according to the invention, preferably 1500 bp at the 5' end and 100 bp at the 3' end.

Further terms used in the description are now defined at this point.

"Affinity tag": this refers to a peptide or polypeptide whose coding nucleic acid sequence can be fused to the nucleic acid sequence according to the invention either directly or by means of a linker, using customary cloning techniques. The affinity tag serves for the isolation, concentration and/or specific purification of the recombinant target protein by means of affinity chromatography from total cell extracts. The abovementioned linker can advantageously comprise a protease cleavage site (for example for thrombin or factor Xa), whereby the affinity tag can be cleaved from the target protein when required. The examples of usual affinity tags are the "His tag" for example from quiagen, hilden, "Strep tag", the "Myc tag" (Invitrogen, Carlsberg), the tag from New England Biolabs which consists of a chitin-binding domain and an inteine, the maltose-binding protein (pMal) from New England Biolabs, and what is known as the CBD tag from Novagen. It this context, the affinity tag can be attached to the 5' or the 3' end of the coding nucleic acid sequence with the sequence encoding the target protein.

"Antisense or cosuppression technique" describes technologies for the suppression (reduction) of gene expression, where a gene encoding a portion (to be defined in the experiment in question) of a natural gene to be suppressed is transformed into a model plant in "sense" or "antisense" orientation under the control of a suitable promoter. As a rule, the suppression of the transcription of the natural gene, which can be detected using suitable methods, is pronounced to a different degree in the transgenic plants generated in this manner. Thus, this technique allows the study of the effects, on an organism, of a gene whose expression has been reduced (for a review, see Trends in Plant Science, 2000, 5(9), 394-396).

"Enzymatic activity/activity assay": the term enzymatic activity describes the ability of an enzyme to convert a substrate into a product. The enzymatic activity can be determined in what is known as an activity assay while the increase in the product, the decrease in the substrate (or starting material) or the decrease in a specific cofactor, or via a combination of at least two of the abovementioned parameters, as a function of a defined period of time.

"Biological activity of a serine hydroxymethyltransferase": For the purposes of the present invention, this term describes that the ability to grow and survive is conferred by the presence of a serine hydroxymethyltransferase, preferably a glyoxysomal serine hydroxymethyltransferase. If the activity of a protein with the biological activity of a glyoxysomal serine hydroxymethyltransferase is inhibited, this leads to reduced growth, cessation of growth or death of the plant.

"Expression cassette": an expression cassette comprises a nucleic acid sequence according to the invention linked operably to at least one genetic control element, such as a promoter, and, advantageously, a further control element, such as a terminator. The nucleic acid sequence of the expression cassette can be for example a genomic or complementary DNA sequence or an RNA sequence, and their semi- or fully synthetic analogs. These sequences can exist in linear or circular form, extrachromosomally or integrated into the genome. The nucleic acid sequences in question can be synthesized or obtained naturally or comprise a mixture of synthetic and natural DNA components, or else consist of various heterologous gene segments of various organisms.

Artificial nucleic acid sequences are also suitable in this context as long as they make possible the expression, in a cell or an organism, of a polypeptide with the biological activity of an SHMT, which polypeptide is encoded by a nucleic acid sequence according to the invention. For example, synthetic nucleotide sequences can be generated which have been optimized with regard to the codon usage of the organisms to be transformed.

All of the abovementioned nucleotide sequences can be generated from the nucleotide units by chemical synthesis in the manner known per se, for example by fragment condensation of individual overlapping complementary nucleotide units of the double helix. Oligonucleotides can be synthesized chemically for example in the manner known per se using the phosphoamidite method (Voet, Voet, $2^{nd}$ Edition, Wiley Press New York, pp. 896-897). When preparing an expression cassette, various DNA fragments can be manipulated in such a way that a nucleotide sequence with the correct direction of reading and the correct reading frame is obtained. The nucleic acid fragments are linked with each other via general cloning techniques as are described, for example, in T. Maniatis, E. F. Fritsch and J. Sambrook, "Molecular Cloning: A Laboratory Manual", Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., "Current Protocols in Molecular Biology", Greene Publishing Assoc. and Wiley-Interscience (1994).

"Operable linkage": an operable, or functional, linkage is understood as meaning the sequential arrangement of regulatory sequences or genetic control elements in such a way that each of the regulatory sequences, or each of the genetic control elements, can fulfill its intended function when the coding sequence is expressed.

"Functional equivalents" describe, in the present context, nucleic acid sequences which hybridize under standard conditions with the nucleic acid sequence SEQ ID NO:3 or parts of the SEQ ID NO:3 and which are capable of bringing about the expression, in a cell or an organism, of a polypeptide with the biological activity of an SHMT. The term functional equivalents accordingly also comprises the nucleic acid sequences SEQ ID NO:7 and also nucleic acid sequences which hybridize with SEQ ID NO:7 or parts of SEQ ID NO:7 and are capable of bringing about the expression, in a cell or an organism, of a polypeptide with the biological activity of an SHMT.

To carry out the hybridization, it is advantageous to use short oligonucleotides with a length of approximately 10-50 bp, preferably 15-40 bp, for example of the conserved or other regions, which can be determined in the manner with which the skilled worker is familiar by comparisons with other related genes. However, longer fragments of the nucleic acids according to the invention with a length of 100-500 bp, or the complete sequences, may also be used for hybridization. Depending on the nucleic acid/oligonucleotide used, for the length of the fragment or the complete sequence, or depending on which type of nucleic acid, i.e. DNA or RNA, is being used for the hybridization, these standard conditions vary. Thus, for example, the melting temperatures for DNA:DNA hybrids are approximately 10° C. lower than those of DNA:RNA hybrids of the same length.

Standard hybridization conditions are to be understood as meaning, depending on the nucleic acid, for example temperatures of between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids are advantageously 0.1×SSC and temperatures of between approximately 20° C. to 65° C., preferably between approximately 30° C. to 45° C. In the case of DNA:RNA hybrids, the hybridization conditions are advantageously 0.1×SSC and temperatures of between approximately 30° C. to 65° C., preferably between approximately 45° C. to 55° C. These hybridization temperatures which have been stated are melting temperature values which have been calculated by way of example for a nucleic acid with a length of approx. 100 nucleotides and a G+C content of 50% in the absence of formamide. The experimental conditions for DNA hybridization are described in specialist textbooks of genetics such as, for example, in Sambrook et al., "Molecular Cloning", Cold Spring Harbor Laboratory, 1989, and can be calculated using formulae with which the skilled worker is familiar, for example as a function of the length of nucleic acids, the type of the hybrids or the G+C content. The skilled worker will find further information on hybridization in the following text books: Ausubel et al. (eds), 1985, "Current Protocols in Molecular Biology", John Wiley & Sons, New York; Hames and Higgins (eds), 1985, "Nucleic Acids Hybridization: A Practical Approach", IRL Press at Oxford University Press, Oxford; Brown (ed), 1991, Essential Molecular Biology: A Practical Approach, IRL Press at Oxford University Press, Oxford.

A functional equivalent of the SEQ ID NO:3 is furthermore also understood as meaning nucleic acid sequences which comprise a part-region which has a defined degree of homology with the SEQ ID NO:3, and furthermore in particular also natural or artificial mutations of the abovementioned nucleic acid sequences which encode a polypeptide with the biological activity of a serine hydroxymethyltransferase. An example of a nucleic acid sequences which comprise a part-region which has a defined degree of identity with the SEQ ID NO:3 is SEQ ID NO:7 and the functional equivalents thereof as defined above.

Thus, the present invention also comprisees, for example, those nucleotide sequences which are obtained by modification of the abovementioned nucleic acid sequences. For example, such modifications can be generated by techniques with which the skilled worker is familiar, such as "Site Directed Mutagenesis", "Error Prone PCR", "DNA-shuffling" (Nature 370, 1994, pp. 389-391) or "Staggered Extension Process" (Nature Biotechnol. 16, 1998, pp. 258-261). The purpose of such a modification can be, for example, the insertion of further cleavage sites for restriction enzymes, the removal of DNA in order to truncate the sequence, the substitution of nucleotides to optimize the codons, or the addition of further sequences. Proteins which are encoded via modified nucleic acid sequences must retain the desired functions despite a deviating nucleic acid sequence.

The term "functional equivalents" can also relate to the amino acid sequence encoded by the nucleic acid sequence in question. In this case, the term "functional equivalent" describes a protein whose amino acid sequence comprisees a part-region which has a defined percentage of at least 91% identity or homology with the SEQ ID NO:4.

Functional equivalents thus comprise naturally occurring variants of the herein-described sequences and artificial nucleic acid sequences, for example those which have been obtained by chemical synthesis and which are adapted to the codon usage, and also the amino acid sequences derived from them.

"Genetic control sequence": the term "genetic control sequence" is considered as equivalent to the term "regulatory sequence". It describes sequences which have an effect on the transcription and, if appropriate translation of the nucleic acids according to the invention in prokaryotic or eukaryotic organisms. Examples are promoters or what are known as "enhancer" sequences. In addition to these control sequences, or instead of these sequences, the natural regulation of these sequences may still be present before the actual structural genes and may, if appropriate, have been genetically modified in such a way that the natural regulation is switched off and the expression of the target gene has been modified, that is to say increased or reduced. The choice of the control sequence depends on the host organism or starting organism. Genetic control sequences furthermore also comprise the 5'-untranslated region, introns or the noncoding 3'-region of genes. Control sequences are furthermore understood as meaning those which make possible homologous recombination or insertion into the genome of a host organism or which permit removal from the genome. Genetic control sequences also comprise further promoters, promoter elements or minimal promoters, and sequences which have an effect on the chromatin structure (for example matrix attachment regions (MARs)), which can modify the expression-governing properties. Thus, genetic control sequences may bring about for example the fact that the tissue-specific expression is additionally dependent on certain stress factors. Such elements have been described, for example, for water stress, abscissic acid (Lam E and Chua N H, J Biol Chem 1991; 266(26): 17131-17135), high- and low-temperature stress (Plant Cell 1994, (6): 251-264) and heat stress (Molecular & General Genetics, 1989, 217(2-3): 246-53).

"Homology" between two nucleic acid sequences or polypeptide sequences is defined by the identity of the nucleic acid sequence/polypeptide sequence over in each case the entire sequence length, which is calculated by alignment with the aid of the program algorithm BESTFIT (Wisconsin Package Version 10.0, University of Wisconsin, Genetics Computer Group (GCG), Madison, USA), setting the following parameters for polypeptides:

| Gap Weight: 8 | Length Weight: 2 |
|---|---|
| Average Match: 2.912 | Average Mismatch: −2.003 | and the following parameters for nucleic acids:

| Gap Weight: 50 | Length Weight: 3 |
|---|---|
| Average Match: 10.000 | Average Mismatch: −9.000 |

In the following text, the term identity is also used synonymously instead of the term "homologous" or "homology".

"Mutations" of nucleic or amino acid sequences comprise substitutions, additions, deletions, inversions or insertions of one or more nucleotide residues, which may also bring about changes in the corresponding amino acid sequence of the target protein by substitution, insertion or deletion of one or more amino acids, and were the functional properties of the target proteins are, in total, essentially retained.

"Natural genetic environment" refers to the natural chromosomal locus in the organism of origin. In the case of a genomic library, the natural genetic environment of the nucleic acid sequence is preferably retained at least in part. The environment flanks the nucleic acid sequence at least 5'- or 3'- and has a sequence length of at least 50 bp, preferably at least 100 bp, especially preferably at least 500 bp, very especially preferably at least 1000 bp, and most preferably at least 5000 bp.

"Plants" for the purposes of the invention are plant cells, plant tissues, plant organs, or intact plants, such as seeds, tubers, flowers, pollen, fruits, seedlings, roots, leaves, stems or other plant parts. Moreover, the term plants is understood as meaning propagation material such as seeds, fruits, seedlings, slips tubers, cuttings or root stocks.

"Reaction time" refers to the time required for carrying out an activity assay until a significant finding regarding an activity is obtained; it depends both on the specific activity of the protein employed in the assay and on the method used and the sensitivity of the operators used. The skilled worker is familiar with the determination of the reaction times. In the case of methods for identifying herbicidally active compounds which are based on photometry, the reaction times are, for example, between >0 to 120 minutes.

"Recombinant DNA" describes a combination of DNA sequences which can be generated by recombinant DNA technology.

"Recombinant DNA technology": generally known techniques for fusing DNA sequences (for example described in Sambrook et al., 1989, Cold Spring Harbor, N.Y., Cold Spring Harbor Laboratory Press).

"Replication origins" ensure the multiplication of the expression cassettes or vectors according to the invention in microorganisms and yeasts, for example the pBR322 ori or the P15A ori in E. coli (Sambrook et al.: "Molecular Cloning. A Laboratory Manual", 2nd ed. Cold Spring Harbor Laboratory Press, Cold Spring Harbor, N.Y., 1989) and the ARS1 ori in yeast (Nucleic Acids Research, 2000, 28(10): 2060-2068).

"Reporter genes" encode readily quantifiable proteins. The transformation efficacy or the transformation site or timing can be assessed by means of these genes via growth assay, fluorescence assay, chemoluminescence assay, bioluminescence assay or resistance assay or via a photometric measurement (intrinsic color) or enzyme activity. Very especially preferred in this context are reporter proteins (Schenborn E, Groskreutz D. Mol Biotechnol. 1999; 13(1): 29-44) such as the "green fluorescent protein" (GFP) (Gerdes H H and Kaether C, FEBS Lett. 1996; 389(1): 44-47; Chui W L et al., Curr Biol 1996, 6: 325-330; Leffel S M et al., Biotechniques. 23(5): 912-8, 1997), chloramphenicol acetyltransferase, a luciferase (Giacomin, Plant Sci 1996, 116: 59-72; Scikantha, J Bact 1996, 178: 121; Millar et al., Plant Mol Biol Rep 1992 10: 324-414), and luciferase genes, in general β-galactosidase or β-glucuronidase (Jefferson et al., EMBO J. 1987, 6, 3901-3907) or the Ura3 gene.

"Selection markers" confer a resistance to antibiotics or other toxic compounds: examples which may be mentioned in this context are the neomycin phosphotransferase gene, which confers resistance to the aminoglycoside antibiotics neomycin (G 418), kanamycin, paromycin (Deshayes A et al., EMBO J. 4 (1985) 2731-2737), the hygro gene (Marsh J L et al., Gene. 1984; 32(3): 481-485), the sul gene (Guerineau F et al., Plant Mol. Biol. 1990; 15(1): 127-136), the hygromycin gene (Gen Bank Accession NO: K 01193) and the she-ble gene, which confers resistance to the bleomycin antibiotic zeocin. Further examples of selection marker genes are genes which confer resistance to 2-deoxyglucose-6-phosphate (WO 98/45456) or phosphinothricin and the like, or those which confer a resistance to antimetabolites, for example the dhfr gene (Reiss, Plant Physiol. (Life Sci. Adv.) 13 (1994) 142-149). Examples of other genes which are suitable are trpB or hisD (Hartman SC and Mulligan RC, Proc Natl Acad Sci USA. 85 (1988) 8047-8051). Another suitable gene is the mannose phosphate isomerase gene (WO 94/20627), the ODC (ornithine decarboxylase) gene (McConlogue, 1987 in: Current Communications in Molecular Biology, Cold Spring Harbor Laboratory, Ed.) or the *Aspergillus terreus* deaminase (Tamura K et al., Biosci Biotechnol Biochem. 59 (1995) 2336-2338).

"Transformation" describes a process for introducing heterologous DNA into a pro- or eukaryotic cell. The term transformed cell describes not only the product of the transformation process per se, but also all of the transgenic progeny of the transgenic organism generated by the transformation.

"Target/target protein": a polypeptide encoded via the nucleic acid sequence according to the invention, which may take the form of an enzyme in the traditional sense or, for example, of a structural protein, development protein, regulatory protein such as transcription factors, kinases, phosphatases, receptors, channel subunits, transport proteins, regulatory subunits which confer substrate or activity regulation to an enzyme complex. All of the targets or sites of action share the characteristic that their functional presence is essential for the survival or the normal development and growth.

"Transgenic": referring to a nucleic acid sequence, an expression cassette or a vector comprising a nucleic acid sequence according to the invention or an organism transformed with the abovementioned nucleic acid sequence, expression cassette or vector, the term transgenic describes all those constructs which have been generated by genetic engineering methods in which either the nucleic acid sequence of the target protein or a genetic control sequence linked operably to the nucleic acid sequence of the target protein or a combination of the abovementioned possibilities are not in their natural genetic environment or have been modified by recombinant methods. In this context, the modification can be achieved, for example, by mutating one or more nucleotide residues of the nucleic acid sequence in question.

The polypeptides encoded by the nucleic acid sequences according to the invention display the biological activity of a pyridoxal-phosphate-dependent serine hydroxymethyl-transferase (SHMT; E. C. 2.1.2.1). SHMTS are found in virtually all types of cells. The enzyme was first isolated from rabbit liver (Schirch & Mason, JBC 238, pp. 1032-1037, 1963) and since then from a large number of organisms such as, for example, plants.

Inhibitors for plant SHMTs have not been described as yet. SHMT from *Euglena gracilis* can be inhibited by millimolar concentrations of various amino acids (for example glycin, serine, cystein) (Sakamoto et al., Agricultural and Biological Chemistry, 1991, 55(9), 2243-2249). Micromolar concentrations of the amino acid analog O-amino-D-serine have an inhibitory effect on ovine SHMT (Baskaran et al., Biochemistry, 1989, 28(25), 9607-9612). It is furthermore known that mimosine, a plant amino acid, can be bound to SHMT from CHO cells by means of photo-linkage, but does not inhibit it (Lin et al. JBC 271, pp. 2548-2556, 1996).

A cytosolic and a mitochondrial form of SHMT, which are involved in different metabolic pathways, can be distinguished in plants. In addition, the existence of a plastid SHMT has been postulated (Douce et al. Trends in Plant Science 6, pp. 167-176, 2001). The cytosolic form of SHMT participates in providing C1 units for the purin and methionin metabolism by catalyzing the reversible reaction from serine to glycin. An ovine cytosolic SHMT protein sequence, which has 55.09% identity with the SEQ ID NO:4, is found under the Gen Bank Acc. No. P35623.

In *Arabidopsis*, five SHMT genes (SHM1-5) have been found; of these, two, SHM1 (Gen Bank Acc. No. AJ271726, Identity to SEQ ID NO:3 78.65%; Gen Bank Acc. No. Q490M9, Identity to SEQ ID NO:4 83.71%) and SHM2 (Gen Bank Acc. No. Q04952; Identity to SEQ ID NO:4 83.62%), are probably localized in the mitochondria, while SHM3, SHM4 and SHM5 constitute cytosolic forms (Mc-Clung et al. Plant Physiol. 123, pp381-391, 2000). A mitochondrial SHMT from pea mitochondria has furthermore been described (*Pisum sativum*; Gen Bank Acc. No. P34899, Identity to SEQ ID NO:4 83.52%; Turner et al. JBC 267, pp. 13528-13534, 1992). Sequences encoding mitochondrial SHMT are also known from *Solanum tuberosum* (Gen Bank Acc. No. Z25863 Identity to SEQ ID NO:3 90.62%, Identity to SEQ ID NO:4 90.45%; Identity to SEQ ID NO:7 86.8%) and from Flayeria pringlei (Gen Bank Acc. No. P49358, Identity to SEQ ID NO:4 86.44%). Moreover, a *Lycopersicon esculentum* EST nucleic acid sequence, which probably likewise includes a mitochondrial SHMT, also exists (Gen Bank Acc. No. AW040079, Identity to SEQ ID NO:3 90.056%).

*Arabidopsis thaliana* mutants in whose mitochondria no SHMT activity has been detected biochemically (stm plants) are described in the literature. In these mutants, photosynthesis is inhibited under ambient $CO_2$ concentrations, and the plants are not viable. While the stm plants are only fully viable under increased $CO_2$ concentrations, they become chlorotic after being transferred to ambient $CO_2$ concentrations, and some of them die (Somerville and Somerville, Plant Physiol. 67, 1981, pp. 666-671; Somerville and Somerville, J. Exp. Bot. 34, 1983, 415-424). The mitochondrial SHM gene of the stm plants which carries the mutation is not known. SHM1 transcript size and quantity are unaltered in stm mutants in comparison with the wild type. According to Beckmann et al. (Planta 202, pp. 379-386, 1997), a possible loss-of-function mutation of the SHM1 gene is probably not responsible for the phenotype of the mutants since this is compensated for by the second SHMT, viz. SHM2. The fact that the mitochondrial SHMT is essential in plants, and could therefore constitute a suitable target for herbicides, has thus not yet been proven unambiguously.

Surprisingly, it has been found within the scope of the present invention that the gene products which are encoded via nucleic acids which comprise the SEQ ID NO:3 are suitable as targets for herbicides. The proof was provided in each case by a targeted reduction in the expression of the target protein in question in Nicotiana tabacum. These plants have phenotypes which are comparable with phenotypes generated by the application of herbicides. Among the symptoms observed were growth retardation and chlorotic leaves, in some cases, the death of entire plants, or of plant parts.

The present invention relates to plant SHMTs, hereinbelow simply referred to as "SHMTs" for the sake of simplicity, preferably mitochondrial SHMTs, and their use as novel target for herbicide. The term "SHMT" accordingly preferably describes mitochondrial SHMT. Claimed within the present scope are nucleic acid sequences which encode a polypeptide with the biological activity of an SHMT, the nucleic acids comprising
a) a nucleic acid sequence with the nucleic acid sequence shown in SEQ ID NO:3; or
b) a nucleic acid sequence which, on the basis of the degeneracy of the genetic code, can be derived from the amino acid sequence shown in SEQ ID NO:4 by back translation; or
c) functional equivalents of the nucleic acid sequence SEQ ID NO:3 comprising a part-region with at least 91% identity to the SEQ ID NO:3.

Preferred in this context are nucleic acid sequences which encode a mitochondrial SHMT. An example of a nucleic acid sequence according to c) is the SEQ ID NO:7 which comprises a part-region having 100% identity to the SEQ ID NO:3. Hence claimed within the scope of the present invention are also nucleic acid sequences which encode a polypeptide with the biological activity of an SHMT, comprising
a) a nucleic acid sequence with the nucleic acid sequence shown in SEQ ID NO:7; or
b) a nucleic acid sequence which, on the basis of the degeneracy of the genetic code, can be derived from the amino acid sequence shown in SEQ ID NO:8 by back translation; or
c) functional equivalents of the nucleic acid sequence SEQ ID NO:7 with at least 88% identity to the SEQ ID NO:7.

As emerges from the definition of the term SHMT, preferred in this context are also nucleic acid sequences which encode a mitochondrial SHMT.

The abovementioned nucleic acid sequences are hereinbelow referred to as "nucleic acid sequences according to the invention".

Reduced amounts of polypeptides encoded by nucleic acid sequences according to the invention cause growth retardation and chlorotic leaves in plants. A reduction in the polypeptide means that the amount of polypeptide is reduced via recombinant methods. A plant which has been modified thus is compared with a plant which has not been genetically modified with regard to this polypeptide, but which is otherwise identical with the genotype of the genetically manipulated plant under identical growth conditions.

The present invention also relates to the gene products of the nucleic acids according to the invention, which constitute novel targets for herbicides which are suitable for controlling undesired plants.

Undesired plants are understood as meaning, in the broadest sense, all those plants which grow at locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds from the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

The functional equivalents of the SEQ ID NO:3 comprise a part-region with at least 91%, preferably at least 92%, 93% and 94%, preferably at least 95% or 96%, especially preferably at least 97% or 98%, very especially preferably at least 99%, identity with the SEQ ID No:3.

The functional equivalents of the SEQ ID NO:4 comprise a part-region with at least 91%, preferably at least 92%, 93% and 94%, preferably at least 95% or 96%, especially preferably at least 97% or 98%, very especially preferably at least 99%, identity with the SEQ ID No:3.

The functional equivalents of the SEQ ID NO:7 have at least 88%, 89%, 90%, preferably at least 91%, 92%, 93%, 94%, 95%, particularly preferably at least 96%, 97%, 98%, 99%, identity with the SEQ ID NO:7.

The SEQ ID NO:3 or parts of the SEQ ID NO:3 can be used for the preparation of hybridization probes, by means of which the corresponding full-length genes can be isolated. Likewise the SEQ ID NO:7 or parts of the SEQ ID NO:7 can be used. The preparation of these probes and the experimental procedure is known. For example, this can be effected via the tailor-made preparation of radioactive or nonradioactive probes by PCR and the use of suitably labeled oligonucleotides, followed by hybridization experiments. The technologies required for this purpose are given, for example, in T. Maniatis, E. F. Fritsch and J. Sambrook, "Molecular Cloning: A Laboratory Manual", Cold Spring Harbor Laboratory, Cold Spring Harbor, N.Y. (1989). The probes in question can furthermore be modified by standard technologies (Lit. SDM or random mutagenesis) that they can be employed for further purposes, for example as probe which hybridizes specifically with mRNA and the corresponding coding sequences in order to analyze the corresponding sequences in other organisms.

Moreover, the abovementioned probes can be used for the detection and isolation of functional equivalents of the SEQ ID NO:3 (or SEQ ID NO:7) from other plant species on the basis of sequence identities. In this context, part or all of the sequence of the SEQ ID NO:3 (or SEQ ID NO:7) in question is used as probe for screening a genomic or cDNA library of the plant species in question or in a computer search for sequences of functional equivalents in electronic databases.

Preferred plant species are the undesired plants which have already been mentioned at the outset.

The invention furthermore relates to expression cassettes comprising a) genetic control sequences in operable linkage with a nucleic acid sequence according to the invention; or
b) additional functional elements; or
c) a combination of a) and b).

The invention furthermore relates to the use of the above-shown expression cassette and to the use of expression cassettes comprising the abovementioned components a) and b) or c), wherein the nucleic acid sequence of a) comprises a part-region with at least 60%, preferably at least 61%, 62%, 63%, 64%, 65%, 66%, 67%, 68%, 69% and 70%, by preference at least 71%, 72%, 73%, 74%, 75%, 76%, 77%, 78%, 79%, 80%, especially preferably at least 81%, 82%, 83%, 84%, 85%, 86%, 87%, 88%, 89%, 90%, very especially preferably at least 91%, 92%, 93%, 94%, 95%, 96%, 97%, 98%, 99% identity with the SEQ ID NO:3, for expressing an SHMT which can be used in in-vitro assay systems. The abovementioned nucleic acid sequence of a), which comprise a part-region having at least 60% identity with the SEQ ID No:3, therefore also comprise functional equivalents of the SEQ ID NO:7 with an identity of at least 46%, 47%, 48%, 49%, 50%, 51%, 52%, 53%, 54%, 55%, 56%, 57%, 58%, 59%, with preference at least 60%, 61%, 62%, 63%, 64%, 65%, 66%, 67%, 68%, 69% and 70%, preferably at least 71%, 72%, 73%, 74%, 75%, especially preferably at least 76%, 77%, 78%, 79%, 80%, 81%, 82%, 83%, 84%, 85%, 86%, 87%, 88%, 89%, very especially preferably at least 90%, 91%, 92%, 93%, 94%, 95%, 96%, 97%, 98%, 99%. Both embodiments of the above-described expression cassettes are hereinbelow termed expression cassette according to the invention.

In a preferred embodiment, an expression cassette according to the invention comprises a promoter at the 5' end of the coding sequence and, at the 3' end, a transcription termination signal and, if appropriate, further genetic control sequences which are linked operably with the interposed nucleic acid sequence encoding an SHMT.

The expression cassettes according to the invention are also understood as meaning analogs which can be brought about, for example, by a combination of the individual nucleic acid sequences on a polynucleotide (multiple constructs), on a plurality of polynucleotides in a cell (cotransformation) or by sequential transformation.

Advantageous genetic control sequences under item a) for the expression cassettes according to the invention or for vectors comprising expression cassettes according to the invention are, for example, promoters such as the cos, tac, trp, tet, lpp, lac, lacIq, T7, T5, T3, gal, trc, ara, SP6, λ-PR or the λ-PL promoter, all of which can be used for expressing SHMT in Gram-negative bacterial strains.

Examples of further advantageous genetic control sequences are present, for example, in the promoters amy and SPO2, both of which can be used for expressing SHMT in Gram-positive bacterial strains, and in the yeast or fungal promoters ADC1, MFa, AC, P-60, CYC1, GAPDH, TEF, rp28, ADH, AOX1 and GAP all of which can be used for expressing SHMT in yeast strands.

Examples of genetic control sequences which are suitable for expression in insect cells are the polyhedrin promoter and the p10 promoter (Luckow, V. A. and Summers, M. D. (1988) Bio/Techn. 6, 47-55).

Advantageous genetic control sequences for expressing SHMT in cell culture are, in addition to polyadenylation sequences such as, for example, from Simian Virus 40 eukaryotic promoters of viral origin such as, for example, promoters of the polyoma virus, adenovirus 2, cytomegalovirus or simian virus 40.

Further advantageous genetic control sequences for expressing SHMT in plants are present in the plant promoters CaMV/35S [Franck et al., Cell 21(1980) 285-294], PRP1 [Ward et al., Plant. Mol. Biol. 22 (1993)], SSU, OCS, LEB4, USP, STLS1, B33, NOS; FBPaseP (WO 98/18940) or in the ubiquitin or phaseolin promoter; a promoter which is preferably used being, in particular, a plant promoter or a promoter derived from a plant virus. Especially preferred are promoters of viral origin such as the promoter of the cauliflower mosaic virus 35S transcript (Franck et al., Cell 21 (1980), 285-294; Odell et al., Nature 313 (1985), 810-812). Further preferred constitutive promoters are, for example, the Agrobacterium nopalinsynthase promoter, the TR double promoter, the agrobacterium OCS (octopine synthase) promoter, the ubiquitin promoter, (Holtorf S et al., Plant Mol Biol 1995, 29: 637-649), the promoters of the vacuola ATPase subunits, or the promoter of a wheat proline-rich protein (WO 91/13991).

The expression cassettes may also comprise, as genetic control sequence, a chemically inducible promoter, by which the expression of the exogenous gene in the plant can be controlled at a specific point in time. Such promoters, such as, for example, the PRP1 promoter (Ward et al., Plant. Mol. Biol. 22 (1993), 361-366), a salicylic-acid-inducible promoter (WO 95/19443), a benzenesulfonamide-inducible promoter (EP-A-0388186), a tetracyclin-inducible promoter (Gatz et al., (1992) Plant J. 2, 397404), an abscissic-acid-inducible promoter (EP-A 335528) or an ethanol- or cyclohexanone-inducible promoter (WO 93/21334) may also be used.

Furthermore, suitable promoters are those which confer tissue- or organ-specific expression in, for example, anthers, ovaries, inflorescences and floral organs, leaves, stomata, trichomes, stems, vascular tissues, roots and seeds. Others which are suitable in addition to the abovementioned constitutive promoters are, in particular, those promoters which ensure leaf-specific expression. Promoters which must be mentioned are the potato cytosolic FBPase promoter (WO 97/05900), the rubisco (ribulose-1,5-bisphosphate carboxylase) SSU (small subunit) promoter or the ST-LSI promoter from potato (Stockhaus et al., EMBO J. 8 (1989), 2445-245). Promoters which are furthermore preferred are those which control expression in seeds and plant embryos. Examples of seed-specific promoters are the phaseolin promoter (U.S. Pat. No. 5,504,200, Bustos M M et al., Plant Cell. 1989; 1(9):839-53), the promoter of the 2S albumin gene (Joseffson L G et al., J Biol Chem 1987, 262: 12196-12201), the legumin promoter (Shirsat A et al., Mol Gen Genet. 1989; 215(2): 326-331), the USP (unknown seed protein) promoter (Bäumlein H et al., Molecular & General Genetics 1991, 225(3): 459-67), the napin gene promoter (Stalberg K, et al., L. Planta 1996, 199: 515-519), the sucrose binding protein promoter (WO 00/26388) or the LeB4 promoter (Bäumlein H et al., Mol Gen Genet 1991, 225: 121-128; Fiedler, U. et al., Biotechnology (NY) (1995), 13 (10) 1090).

Further promoters which are suitable as genetic control sequences are, for example, specific promoters for tubers, storage roots or roots, such as, for example, the class I patatin promoter (B33), the potato cathepsin D inhibitor promoter, the starch synthase (GBSS1) promoter or the sporamin promoter, fruit-specific promoters such as, for example, the fruit-specific promoter from tomato (EP-A 409625), fruit-maturation-specific promoters such as, for example, the fruit-maturation-specific promoter from tomato (WO 94/21794), inflorescence-specific promoters such as, for example, the phytoene synthase promoter (WO 92/16635) or the promoter of the P-rr gene (WO 98/22593), or specific plastid chromoplast promoters such as, for example, the RNA polymerase promoter (WO 97/06250), or else the *Glycine max* phosphoribosyl-pyrophosphate amidotransferase promoter (see also Genbank Accession No. U87999), or another node-specific promoter as described in EP-A 249676.

Additional functional elements b) are understood as meaning by way of example but not by limitation reporter genes, replication origins, selection markers and what are known as affinity tags, in fusion with SHMT direct or by means of a linker optionally comprising a protease cleavage site. Further suitable additional functional elements are sequences which ensure that the product is targeted into the apoplasts, into plastids, the vacuole, the mitochondrion, the peroxisome, the endoplasmatic reticulum (ER) or, owing to the absence of such operative sequences, remains in the compartment where it is formed, the zytosol, (Kermode, Crit. Rev. Plant Sci. 15, 4 (1996), 285-423).

Also in accordance with the invention are vectors comprising at least one copy of the nucleic acid sequences according to the invention and/or the expression cassettes according to the invention.

In addition to plasmids, vectors are furthermore also understood as meaning all of the other known vectors with which the skilled worker is familiar, such as, for example, phages, viruses such as SV40, CMV, baculovirus, adenovirus, transposons, IS elements, phasmids, phagemids, cosmids or linear or circular DNA. These vectors can be replicated autonomously in the host organism or replicated chromosomally; chromosomal replication is preferred.

In a further embodiment of the vector, the nucleic acid construct according to the invention can advantageously also be introduced into the organisms in the form of a linear DNA and integrated into the genome of the host organism via heterologous or homologous recombination. This linear DNA may consist of a linearized plasmid or only of the nucleic acid construct as vector, or the nucleic acid sequences used.

Further prokaryotic or eukaryotic expression systems are mentioned in Chapters 16 and 17 in Sambrook et al., "Molecular Cloning: A Laboratory Manual." 2nd, ed., Cold Spring Harbor Laboratory, Cold Spring Harbor Laboratory Press, Cold Spring Harbor, N.Y., 1989. Further advantageous vectors are described in Hellens et al. (Trends in plant science, 5, 2000).

The expression cassette according to the invention and vectors derived therefrom can be used for transforming bacteria, *cyanobacteria*, yeasts, filamentos fungi and algae and eukaryotic nonhuman cells (for example insect cells) with the aim of producing SHMT recombinantly, the generation of a suitable expression cassette depending on the organism in which the gene is to be expressed.

In a further advantageous embodiment, the nucleic acid sequences used in the method according to the invention may also be introduced into an organism by themselves.

If, in addition to the nucleic acid sequences, further genes are to be introduced into the organism, they can all be introduced into the organism together in a single vector, or each individual gene can be introduced into the organism in in each case one vector, it being possible to introduce the different vectors simultaneously or in succession.

In this context, the introduction, into the organisms in question (transformation), of the nucleic acid(s) according to the invention, of the expression cassette or of the vector can be effected in principle by all methods with which the skilled worker is familiar.

In the case of microorganisms, the skilled worker will find suitable methods in the textbooks by Sambrook, J. et al. (1989) "Molecular cloning: A laboratory manual", Cold Spring Harbor Laboratory Press, von F. M. Ausubel et al. (1994) "Current protocols in molecular biology", John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Habor Laboratory Press or Guthrie et al. "Guide to Yeast Genetics and Molecular Biology", Methods in Enzymology, 1994, Academic Press.

In the case of dicots, the methods which have been described for the transformation and regeneration of plants from plant tissues or plant cells can be exploited for transient or stable transformation. Suitable methods are the biolistic method or the transformation of protoplasts (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge), electroporation, the incubation of dry embryos in DNA-comprising solution, microinjection and the *agrobacterium*-radiated gene transfer. The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993) 128-143 and in Potrykus, Annu. Rev. Plant Physiol. Plant Molec. Biol. 42 (1991) 205-225).

The transformation by means of *agrobacteria*, and the vectors to be used for the transformation, are known to the skilled worker and described extensively in the literature (Bevan et al., Nucl. Acids Res. 12 (1984) 8711. The intermediary vectors can be integrated into the agrobacterial Ti or Ri plasmid by means of homologous recombination owing to sequences which are homologous to sequences in the T-DNA. This plasmid additionally comprises the vir region, which is required for the transfer of the T-DNA. Intermediary vectors are not capable of replication in *agrobacteria*. The intermediary vector can be transferred to *Agrobacterium tumefaciens* by means of a helper plasmid (conjugation). Binary vectors are capable of replication both in *E. coli* and in *agrobacteria*. They comprise a selection of marker gene and a linker or polylinker which are framed by the right and left T-DNA border region. They can be transformed directly into the *agrobacteria* (Holsters et al. Mol. Gen. Genet. 163 (1978), 181-187), EP A 0 120 516; Hoekema, In: The Binary Plant Vector System Offsetdrukkerij Kanters B. V., Alblasserdam (1985), Chapter V; Fraley et al., Crit. Rev. Plant. Sci., 4: 1-46 and An et al. EMBO J. 4 (1985), 277-287).

The transformation of monocots by means of vectors based on grobacterium has also been described (Chan et al, Plant Mol. Biol. 22(1993), 491-506; Hiei et al, Plant J. 6 (1994) 271-282; Deng et al; Science in China 33 (1990), 28-34; Wilmink et al, Plant Cell Reports 11, (1992) 76-80; May et al; Biotechnology 13 (1995) 486-492; Conner and Domisse; Int. J. Plant Sci. 153 (1992) 550-555; Ritchie et al; Transgenic Res. (1993) 252-265). Alternative systems for the transformation of monocots are the transformation by means of biolistic approach (Wan and Lemaux; Plant Physiol. 104 (1994), 37-48; Vasil et al; Biotechnology 11 (1992), 667-674; Ritala et al, Plant Mol. Biol. 24, (1994) 317-325; Spencer et al, Theor. Appl. Genet. 79 (1990), 625-631), protoplast transformation, the electroporation of partially permeabilized cells, and the introduction of DNA by means of glass fibers. In particular the transformation of maize has been described repeatedly in the literature (WO 95/06128; EP 0513849 A1; EP 0465875 A1; EP 0292435 A1; Fromm et al, Biotechnology 8 (1990), 833-844; Gordon-Kamm et al, Plant Cell 2 (1990), 603-618; Koziel et al, Biotechnology 11(1993) 194-200; Moroc et al, Theor Applied Genetics 80 (190) 721-726).

The successful transformation of other cereal species has also already been described for example in the case of barley (Wan and Lemaux, see above; Ritala et al, see above; wheat (Nehra et al, Plant J. 5(1994) 285-297).

*Agrobacteria* which have been transformed with a vector according to the invention can likewise be used in a known manner for the transformation of plants, such as test plants like *Arabidopsis* or crop plants like cereals, maize, oats, rye, barley, wheat, soya, rice, cotton, sugarbeet, canola, sunflower, flax, hemp, potato, tobacco, tomato, carrot, *capsicum*, oilseed rape, tapioca, cassava, arrowroot, Tagetes, alfalfa, lettuce and the various tree, nut and grapevine species, for example by bathing scarified leaves or leaf segments in an agrobacterial solution and subsequently growing them in suitable media.

The genetically modified plant cells can be regenerated via all methods with which the skilled worker is familiar. Such methods can be found in the abovementioned publications by S. D. Kung and R. Wu, Potrykus or Höfgen and Willmitzer.

The transgenic organisms generated by transformation with one of the above-described embodiments of an expression cassette comprising a nucleic acid sequence according to the invention or a vector comprising the abovementioned expression cassette, and the recombinant SHMT which can be obtained from the transgenic organism by means of expression, are subject matter of the present invention. The use of transgenic organisms comprising an expression cassette according to the invention, for example for providing recombinant protein, and/or the use of these organisms in in-vivo assay systems are likewise subject matter of the present invention.

Preferred organisms for the recombinant expression are not only bacteria, yeasts, mosses, algae and fungi, but also eukaryotic cell lines.

Preferred mosses are *Physcomitrella patens* or other mosses described in Kryptogamen [Cryptogamia], Vol. 2, Moose, Farne [Mosses, Ferns], 1991, Springer Verlag (ISBN 3540536515).

Preferred within the bacteria are, for example, bacteria from the genus *Escherichia, Erwinia, Flavobacterium, Alcaligenes* or *cyanobacteria*, for example from the genus *Synechocystis* or *Anabena*.

Preferred yeasts are *Candida, Saccharomyces, Schizosaccheromyces, Hansenula* or *Pichia*.

Preferred fungi are *Aspergillus, Trichoderma, Ashbya, Neurospora, Fusarium, Beauveria, Mortierella, Saprolegnia, Pythium*, or other fungi described in Indian Chem Engr. Section B. Vol 37, No 1, 2 (1995).

Preferred plants are selected in particular among monocotyledonous crop plants such as, for example, cereal species such as wheat, barley, sorghum or millet, rye, triticale, maize, rice or oats, and sugarcane. The transgenic plants according to the invention are, furthermore, in particular selected from among dicotyledonous crop plants such as, for example, Brassicaceae such as oilseed rape, cress, *Arabidopsis*, cabbages or canola; Leguminosae such as soyabean, alfalfa, pea, beans or peanut, Solanaceae such as potato, tobacco, tomato, egg plant or *capsicum*; Asteraceae such as sunflower, Tagetes, lettuce or *Calendula*; Cucurbitaceae such as melon, pumpkin/squash or zucchini, or linseed, cotton, hemp, flax, red pepper, carrot, carrot, sugar beet, or various tree, nut and grapevine species.

In principle, transgenic animals such as, for example, *C. elegans*, are also suitable as host organisms.

Also preferred is the use of expression systems and vectors which are available to the public or commercially available.

Those which must be mentioned for use in *E. coli* bacteria are the typical advantageous commercially available fusion and expression vectors pGEX [Pharmacia Biotech Inc; Smith, D. B. and Johnson, K. S. (1988) Gene 67: 31-40], pMAL (New England Biolabs, Beverly, Mass.) and pRIT5 (Pharmacia, Piscataway, N.J.), which comprises glutathion S transferase (GST), maltose binding protein or protein A, the pTrc vectors (Amann et al., (1988) Gene 69: 301-315), "pKK233-2" by CLONTECH, Palo Alto, Calif. and the "pET"-, and the "pBAD" vector series from Stratagene, La Jolla.

Further advantageous vectors for use in yeast are pYepSec1 (Baldari, et al., (1987) Embo J. 6: 229-234), pMFa (Kurjan and Herskowitz, (1982) Cell 30: 933-943), pJRY88 (Schultz et al., (1987) Gene 54: 113-123), and pYES derivatives, pGAPZ derivatives, pPICZ derivatives, and the vectors of the "*Pichia* Expression Kit" (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

As an alternative, insect cell expression vectors may also be used advantageously, for example for expression in Sf9, Sf21 or Hi5 cells, which are infected via recombinant Baculoviruses. Examples of these are the vectors of the pAc series (Smith et al. (1983) Mol. Cell Biol. 3: 2156-2165) and the pVL series (Lucklow and Summers (1989) Virology 170: 31-39). Others which may be mentioned are the Baculovirus expression systems "MaxBac 2.0 Kit" and "Insect Select System" by Invitrogen, Carlsbad or "BacPAK Baculovirus Expression System" by CLONTECH, Palo Alto, Calif. Insect cells are particularly suitable for overexpressing eukaryotic proteins since they effect posttranslational modifications of the proteins which are not possible in bacteria and yeasts. The skilled worker is familiar with the handling of cultured insect cells and with their infection for expressing proteins, which can be carried out analogously to known methods (Luckow and Summers, Bio/Tech. 6, 1988, pp. 47-55; Glover and Hames (eds) in DNA Cloning 2, A practical Approach, Expression Systems, Second Edition, Oxford University Press, 1995, 205-244).

Plant cells or algal cells are others which can be used advantageously for expressing genes. Examples of plant expression vectors can be found as mentioned above in Becker, D., et al. (1992) "New plant binary vectors with selectable markers located proximal to the left border", Plant Mol. Biol. 20: 1195-1197 or in Bevan, M. W. (1984) "Binary *Agrobacterium* vectors for plant transformation", Nucl. Acid. Res. 12: 8711-8721.

Moreover, the nucleic acid sequences according to the invention can be expressed in mammalian cells. Examples of suitable expression vectors are pCDM8 and pMT2PC, which are mentioned in: Seed, B. (1987) Nature 329: 840 or Kaufman et al. (1987) EMBO J. 6: 187-195). Promoters preferably to be used in this context are of viral origin such as, for example, promoters of polyoma virus, adenovirus 2, cytomegalovirus or simian virus 40. Further prokaryotic and eukaryotic expression systems are mentioned in Chapter 16 and 17 in Sambrook et al., Molecular Cloning: A Laboratory Manual. 2nd, ed., Cold Spring Harbor Laboratory, Cold Spring Harbor Laboratory Press, Cold Spring Harbor, N.Y., 1989. Further advantageous vectors are described in Hellens et al. (Trends in plant science, 5, 2000).

All of the above-described embodiments of the transgenic organisms come under the term "transgenic organism according to the invention".

The present invention furthermore relates to the use of nucleic or amino acid sequences of SHMTs in a method for identifying herbicidally active test compounds. As already mentioned further above, the term "SHMT" preferably comprises mitochondrial SHMT. All methods for identifying herbicidally active inhibitors are hereinbelow referred to as methods according to the invention.

The use forms, of methods according to the invention, which are now described in the following text are preferably based on the use of SHMTs which are encoded via a nucleic acid sequence comprising
a) a nucleic acid sequence according to the invention; or
b) a functional equivalent of the nucleic acid sequence SEQ ID NO:3 which comprisees a part-region which has at least 60%, preferably at least 61%, 62%, 63%, 64%, 65%, 66%, 67%, 68%, 69% and 70%, preferably at least 71%, 72%, 73%, 74%, 75%, 76%, 77%, 78%, 79%, 80%, especially preferably at least 81%, 82%, 83%, 84%, 85%, 86%, 87%, 88%, 89%, 90%, very especially preferably at least 91%, 92%, 93%, 94%, 95%, 96%, 97%, 98%, 99% identity with the SEQ ID NO:3.

The abovementioned nucleic acid sequence of b), which comprise a part-region with at least 60% identity with the SEQ ID NO:3, accordingly also comprise functional equivalents of the SEQ ID NO:7 with at leat 46%, 47%, 48%, 49%, 50%, 51%, 52%, 53%, 54%, 55%, 56%, 57%, 58%, 59%, with preference at least 60%, 61%, 62%, 63%, 64%, 65%, 66%, 67%, 68%, 69% and 70%, preferably at least 71%, 72%, 73%, 74%, 75%, especially preferably at least 76%, 77%, 78%, 79%, 80%, 81%, 82%, 83%, 84%, 85%, 86%, 87%, 88%, 89%, very especially preferably at least 90%, 91%, 92%, 93%, 94%, 95%, 96%, 97%, 98%, 99% identity. The nucleic acid sequence of b) a polypeptide with the enzymatic, preferably biological, activity of an SHMT.

The method according to the invention for identifying herbicidally active substances comprising the following steps:
i. bringing a nucleic acid molecule encoding a polypeptide with the enzymatic, preferably biological, activity of a serine hydroxymethyltransferase, preferably of a mitochondrial serine hydroxymethyltransferase, or of the polypeptide encoded by the nucleic acid molecule into contact with one or more test compounds under conditions which permit the test compound(s) to bind to the nucleic acid molecule or the polypeptide which is encoded via the nucleic acid; and
ii. detecting whether the test compound binds to the polypeptide of i); or
iii. detecting whether the test compound reduces or blocks the activity of the polypeptide or of i); or
iv. detecting whether the test compound reduces or blocks the transcription, translation or expression of the nucleic acid of i).

Preferred methods according to the invention for identifying herbicidally active compounds comprise the following steps:

i. bringing the nucleic acid molecule as defined above, or the polypeptide encoded by the nucleic acid molecule, into contact with one or more test compounds under conditions which permit binding of the test compound(s) to the nucleic acid molecule or the polypeptide encoded via the nucleic acid; and
ii. detecting whether the test compound binds to the polypeptide of i); or
iii. detecting whether the test compound reduces or blocks the activity of the polypeptide of i); or
iv. detecting whether the test compound reduces or blocks the transcription, translation or expression of the nucleic acid of i).

The detection in accordance with step (ii) of the above method can be effected using techniques which identify the interaction between protein and ligand. In this context, either the test compound or the enzyme can comprise the detectable label such as, for example, a fluorescent label, a radioisotrope, a chemiluminescent label or an enzyme label. Examples of enzyme labels are horseradish peroxidase, alkaline phosphatase or luciferase. The subsequent detection depends on the label and is known to the skilled worker.

In this context, five preferred embodiments which are also suitable for high-throughput methods (HTS) in connection with the present invention, must be mentioned in particular:
1. The average diffusion rate of a fluorescent molecule as a function of the mass can be determined in a small sample volume via fluorescence correlation spectroscopy (FCS) (Proc. Natl. Acad. Sci. USA (1994) 11753-11575). FCS can be employed for determining protein/ligand interaction by measuring the changes in the mass, or the changed diffusion rate which this entails, of a test compound when binding to SHMT. A method according to the invention can be designed directly for measuring the binding of a test compound labeled by a fluorescent molecule. As an alternative, the method according to the invention can be designed in such a way that a chemical reference compound which is labeled by a fluorescent molecule is displaced by further test compounds ("displacement assay"). The compounds which are identified in this manner may be suitable as inhibitors.
2. Fluoresence polarization exploits the characteristic of a quiescent fluorophore excited with polarized light to likewise emit polarized light. If, however, the fluorophore is allowed to rotate during the excited state, the polarization of the fluorescent light which is emitted is more or less lost. Under otherwise identical conditions (for example temperature, viscosity, solvent), the rotation is a function of molecule size, whereby findings regarding the size of the fluorophore-bound residue can be obtained via the reading (Methods in Enzymology 246 (1995), pp. 283-300). A method according to the invention can be designed directly for measuring the binding of a fluorescently labeled test compound to the SHMT. As an alternative, the method according to the invention may also take the form of the "displacement assay" described under 1. The compounds identified in this manner may be suitable as inhibitors.
3. Fluorescent resonance energy transfer (FRET) is based on the irradiation-free energy transfer between two spatially adjacent fluorescent molecules under suitable conditions. A prerequisite is that the emission spectrum of the donor molecule overlaps with the excitation spectrum of the acceptor molecule. Using the fluorescent label of SHMT and the test compound, the binding can be measured by means of FRET (Cytometry 34, 1998, pp. 159-179). As an alternative, the method according to the invention may also take the form of the "displacement assay" described under 1. An especially suitable embodiment of FRET technology is "Homogeneous Time Resolved Fluorescence" (HTRF) as can be obtained from Packard BioScience. The compounds which are identified in this manner may be suitable as inhibitors.

4. Surface-enhanced laser desorption/ionization (SELDI) in combination with a time-of-flight mass spectrometer (MALDI-TOF) makes possible the rapid analysis of molecules on a support and can be used for analyzing protein/ligand interactions (Worral et al., (1998) Anal. Biochem. 70:750-756). In a preferred embodiment, SHMT is immobilized on a suitable support and incubated with the test compound. After one or more suitable wash steps, the test compound molecules which are additionally bound to SHMT can be detected by means of the above-mentioned methodology and inhibitors can thus be selected. The compounds which are identified in this manner may be suitable as inhibitors.

5. The measurement of surface plasmon resonance is based on the change in the refractive index at a surface when a test compound binds to a protein which is immobilized to said surface. Since the change in the refractive index is identical for virtually all proteins and polypeptides for a defined change in the mass concentration at the surface, this method can be applied to any protein in principle (Lindberg et al. Sensor Actuators 4 (1983) 299-304; Malmquist Nature 361 (1993) 186-187). The measurement can be carried out for example with the automatic analyzer based on surface plasmon resonance which is available from Biacore (Freiburg) at a throughput of, currently, up to 384 samples per day. A method according to the invention can be designed directly for measuring the binding of a test compound to SHMT. As an alternative, the method according to the invention may also take the form of the "displacement assay" described under 1. The compounds identified in this manner may be suitable as inhibitors.

All of the substances identified via the abovementioned methods can subsequently be checked for their herbicidal action in another embodiment of the method according to the invention.

Furthermore, there exists the possibility of detecting further candidates for herbicidal active ingredients by molecular modeling via elucidation of the three-dimensional structure of SHMT by x-ray structure analysis. The preparation of protein crystals required for x-ray structure analysis, and the relevant measurements and subsequent evaluations of these measurements, the detection of a binding site in the protein, and the prediction of potential inhibitor structures are known to the skilled worker. In principle, an optimization of the compound identified by the abovementioned methods is also possible via molecular modeling.

A preferred embodiment of the method according to the invention, which is based on steps i) and ii), consists in a) expressing an SHMT in a transgenic organism according to the invention, or growing an organism which naturally comprises an SHMT;

b) bringing the SHMT of step a) in the cell digest of the transgenic or nontransgenic organism, in partially purified form or in homogeneously purified form, into contact with a test compound; and c) selecting a compound which reduces or blocks the SHMT activity, the activity of the SHMT incubated with the test compound being compared with the activity of an SHMT not incubated with a test compound.

Based on the abovementioned nucleic acid sequences, the method can, accordingly, comprise a) either expressing, in a transgenic organism, a mitochondrial plant serine hydroxymethyltransferase which is encoded by a nucleic acid sequence comprising a nucleic acid sequence with the nucleic acid sequence shown in SEQ ID NO:3; or a nucleic acid sequence which, on the basis of the degeneracy of the genetic code, can be derived from the amino acid sequence shown in SEQ ID NO:4 by back translation; or functional equivalents of the nucleic acid sequence SEQ ID NO:3, comprising a part-region with at least 91% identity to the SEQ ID NO:3, or a nucleic acid sequence comprising a part-region with at least 60% identity to the SEQ ID NO:3, or culturing an organism which naturally comprises a plant serine hydroxymethyltransferase which is encoded by a nucleic acid sequence comprising a nucleic acid sequence with the nucleic acid sequence shown in SEQ ID NO:3; or a nucleic acid sequence which, on the basis of the degeneracy of the genetic code, can be derived from the amino acid sequence shown in SEQ ID NO:4; or functional equivalents of the nucleic acid sequence SEQ ID NO:3 by back translation, comprising a part-region with at least 91% identity to the SEQ ID NO:3, or a nucleic acid sequence comprising a part-region with at least 60% identity to the SEQ ID NO:3;

b) bringing the serine hydroxymethyltransferase of step a) in the cell digest of the transgenic or nontransgenic organism, in partially purified form or in homogeneously purified form, into contact with a test compound, and c) selecting a test compound which reduces or blocks the activity of the serine hydroxymethyltransferase of step a), the activity of the serine hydroxymethyltransferase incubated with the test compound being compared with the activity of a serine hydroxymethyltransferase which is not incubated with a test compound.

Again, it is evident that the abovementioned nucleic acid sequences of a) which comprise a part-region with at least 60% identity to the SEQ ID No:3, also comprise functional equivalents of the SEQ ID NO:7 with an identity of at least 46%. As regards the functional equivalents, the abovementioned preferences apply.

The solution comprising the SHMT can consist of the lysate of the original organism or of the transgenic organism which has been transformed with an expression cassette according to the invention. If appropriate, the SHMT can be purified partially or fully via customary methods. A general overview over current protein purification techniques is described, for example, in Ausubel, F. M. et al., Current Protocols in Molecular Biology, Greene Publishing Assoc. and Wiley-Interscience (1994); ISBN 0-87969-309-6. If SHMT is obtained recombinantly, the protein which takes the form of a fusion with an affinity tag can be purified via affinity chromatography as is known to the skilled worker. In the in-vitro methods according to the invention, care must be taken that the essential cofactor of SHMT, namely pyridoxal phosphate, is present in a sufficient amount, i.e., as a rule, in the range from 50-600 mm, preferably 80-500 mm, per mol of enzyme.

The SHMT which is required for in-vitro methods can thus be isolated either by means of heterologous expression from a transgenic organism according to the invention or from an organism comprising a polypeptide with SHMT activity, preferably from an undesired plant, the term "undesired plant" being understood as meaning the species mentioned at the outset.

To identify herbicidal compounds, the SHMT is incubated with a test compound. After a reaction time, the SHMT activity is determined by one of the abovementioned methods in comparison with the activity of the uninhibited SHMT. If the polypeptide according to the invention is inhibited, a significant decrease in activity in comparison with the activity of the noninhibited polypeptide according to the invention is observed, the result being a reduction of at least 10%, advantageously at least 20%, preferably at least 30%, especially preferably by at least 50%, up to 100% reduction (blocking). Preferred is an inhibition of at least 50% at test compound concentrations of $10^{-4}$ M, preferably at $10^{-5}$ M, especially preferably of $10^{-6}$ M, based on enzyme concentration in the micromolar range.

The SHMT enzyme activity can be determined for example by an activity assay, i.e. by incubating the SHMT with a suitable substrate and cofactors, with monitoring the conversion of the substrate or of the cofactor. Examples of suitable substrates are serine or glycin, and examples of suitable cofactors tetrahydrofolate or C1-tetrahydrofolate. If appropriate, derivatives of the abovementioned compounds which comprise a detectable label such as, for example, a fluorescent label, a radioisotope label or a chemiluminescent label, may also be used.

For example, the SHMT activity can be measured using a radioactive method according to the invention (Bourguignon et al. Biochem. J. 255, pp. 169-178, 1988).

However, the SHMT enzyme activity can also be determined by means of a chromatographic separation method based on the separation of tetrahydrofolate from C1-tetrahydrofolate, followed by quantitative analysis of the amount of tetrahydrofolate and C1-tetrahydrofolate via integration of the peaks obtained in the chromatography via UV-spectroscopy. The chromatographic separation is preferably effected by reversed-phase chromatography (RPC), for example using an HPLC or FPLC system. The principle of this chromatography and the buffers and apparatuses used for it are known to the skilled worker and are described, for example, in "Introduction to Modern Liquid Chromatography" by L. R. Snyder and J. J. Kirkland, 2nd Edition. John Wiley & Sons, 1979.

As a rule, the mobile phases which are conventionally used in RPC and which are known to the skilled worker are used.

The amounts of substrate (for example serine) to be employed in the activity assay range from 1-50 mM, and the amounts of tetrahydrofolate range from 1-10 mM, based on 1-100 µg/ml enzyme.

In an especially preferred embodiment, the conversion of the substrate is monitored photometrically, using a modification of a method described by Stover and Schirch (Anal. Biochem. 202, pp. 82-88) which is based on coupling the SHMT reaction with the reaction catalyzed by NAD-dependent methylenetetrahydrofolate dehydrogenase (MTD) and photometric measurement at 340 nm.

A preferred embodiment of the method according to the invention which is based on steps i) and iii) consists of the following steps:

a) generating a transgenic organism according to the invention;
b) applying a test substance to the transgenic organism of a) and to a nontransgenic organism of the same type;
c) determining the growth or the viability of the transgenic and the nontransgenic organisms after application of the test substance; and
d) selecting test substances which bring about a reduced growth or a reduced viability of the nontransgenic organism in comparison with the growth of the transgenic organism.

In this context, the difference in growth in step c) for the selection of a herbicidally active inhibitor amounts to at least 10%, preferably 20%, by preference 30%, especially preferably 40% and very especially preferably 50%.

The transgenic organism in this context is a bacterium, a yeast, a fungus, a plant or a eukaryotic cell line, preferably plants, bacteria or yeasts, which can readily be transformed by means of customary techniques, such as *Arabidopsis thaliana, Solanum tuberosum, Nicotiana tabacum, Saccharomyces cerevisiae* or *E. coli*, into which the sequence encoding a polypeptide according to the invention has been incorporated by transformation. These transgenic organisms thus show increased tolerance to compounds which inhibit the polypeptide according to the invention. *E. coli* and *Saccharomyces cerevisiae* are in particular the organisms of choice since their genomes have been sequenced in their entirety and they can readily be used for the generation of "knock-out" mutants (for example Methods in Yeast Genetics, Kaiser, Michaelis, Mitchell (eds.) CSHL Press, Cold Spring Harbor Laboratory Press, 1994: 73-85).

However, the abovementioned method can also be used for identifying substances with a growth-regulatory action. In this context, the transgenic organism employed is a plant. Moreover, step d) involves the selection of test compounds which bring about a modified growth of the nontransgenic organism in comparison with the growth of the transgenic organism. Modified growth is understood as meaning, in this context, inhibition of the vegetative growth of the plants, which can manifest itself in particular in reduced longitudinal growth. Accordingly, the treated plants show stunted growth; moreover, their leaves are darker. In addition, modified growth is also understood as meaning a change of the course of maturation over time, the inhibition of promotion of lateral branched growth of the plants, shortened or extended developmental stages, increased standing ability, the growth of larger amounts of buds, flowers, leaves, fruits, seed kernels, roots and tubers, an increased sugar content in plants such as sugarbeet, sugar cane and citrus fruit, an increased protein content in plants such as cereals or soybean, or stimulation of the latex flow in rubber trees. The skilled worker is familiar with the detection of such modified growth.

It is also possible, in the method according to the invention, to employ a plurality of test compounds in a method according to the invention. If a group of test compounds affect the target, then it is either possible directly to isolate the individual test compounds or to divide the group of test compounds into a variety of subgroups, for example when it consists of a multiplicity of different components, in order to reduce the number of the different test compounds in the method according to the invention. The method according to the invention is then repeated with the individual test compound or the relevant subgroup of test compounds. Depending on the complexity of the sample, the above-described steps can be carried out repeatedly, preferably until the subgroup identified in accordance with the method according to the invention only comprises a small number of test compounds, or indeed just one test compound.

All of the compounds which have been identified via the methods according to the invention can subsequently be tested in vivo for their herbicidal action. One possibility of testing the compounds for herbicidal action is to use duck weed, Lemna minor in microtiter plates. Parameters which can be measured are modifications in the chlorophyll content and the photosynthesis rate. It is also possible to apply the compound directly to undesired plants, it being possible to identify the herbicidal action for example via restricted growth.

The method according to the invention can advantageously also be carried out in high-throughput methods, or high-throughput screening methods (HTS).

HTS makes possible the simultaneous testing of a multiplicity of different compounds.

The use of supports which comprise one or more of the nucleic acid molecules according to the invention, one or more of the vectors comprising the nucleic acid sequence according to the invention, one or more transgenic organisms comprising at least one of the nucleic acid sequences according to the invention or one or more (poly)peptides encoded via the nucleic acid sequences according to the invention lends itself to carrying out an HTS in practice. The support used can be solid or liquid, it is preferably solid and especially preferably a microtiter plate. The abovementioned supports are also the subject matter of the present invention. In accordance with the most widely used technique, 96-well, 384-well and 1536-well microtiter plates which, as a rule, can comprise volumes of 200 µl, are used. Besides the microtiter plates, the further components of an HTS system which match the corresponding microtiter plates, such as a large number of instruments, materials, automatic pipetting devices, robots, automated plate readers and plate washers, are commercially available.

In addition to the HTS systems based on microtiter plates, what are known as "free-format assays" or assay systems where no physical barriers exist between the samples such as, for example, in Jayaickreme et al., Proc. Natl. Acad. Sci U.S.A. 19 (1994) 161418; Chelsky, "Strategies for Screening Combinatorial Libraries, First Annual Conference of The Society for Biomolecular Screening in Philadelphia, Pa. (Nov. 710, 1995); Salmon et al., Molecular Diversity 2 (1996), 5763 and U.S. Pat. No. 5,976,813, may also be used.

The invention furthermore relates to compounds identified by the methods according to the invention. These compounds are hereinbelow referred to as "selective compounds". They have a molecular weight of less than 1000 g/mol, advantageously less than 500 g/mol, preferably less than 400 g/mol, especially preferably less than 300 g/mol. Herbicidally active compounds have a Ki value of less than 1 mM, preferably less than 1 µM, especially preferably less than 0.1 µM, very especially preferably less than 0.01 µM.

Naturally, the compounds identified by the methods according to the invention can also be present in the form of their agriculturally useful salts. Agriculturally useful salts which are suitable are mainly the salts of those cations, or the acid addition salts of those acids, whose cations, or anions, do not adversely affect the herbicidal action of the herbicidally active compounds identified via the methods according to the invention.

If the selected compounds comprise asymmetrically substituted α-carbon atoms, they may furthermore also be present in the form of racemates, enantiomer mixtures, pure enantiomers or, if they have chiral substituents, also in the form of diastereomer mixtures.

The selected compounds can be chemically synthesized substances or substances produced by microbes and can be found, for example, in cell extracts or, for example, plants, animals or microorganisms. The reaction mixture can be a cell-free extract or comprise a cell or cell culture. Suitable methods are known to the skilled worker and are described generally for example in Alberts, Molecular Biology the cell, 3$^{rd}$ Edition (1994), for example chapter 17.

Candidate test compounds can be expression libraries such as, for example, cDNA expression libraries, peptides, proteins, nucleic acids, antibodies, small organic substances, hormones, PNAs or the like (Milner, Nature Medicin 1 (1995), 879-880; Hupp, Cell. 83 (1995), 237-245; Gibbs, Cell. 79 (1994), 193-198 and references cited therein).

The selected compounds can be used for controlling undesired vegetation, if appropriate also for the defoliation of, for example, potatoes or the desiccation of, for example, cotton, and as growth regulators. Herbicidal compositions comprising the selected compounds afford very good control of vegetation on noncrop areas. In crops such as wheat, rice, maize, soybean and cotton, they act against broad-leaved weeds and grass weeds without inflicting any significant damage on the crop plants. This effect is observed in particular at low application rates. The selected compounds can be used for controlling the harmful plants which have already been mentioned above.

Depending on the application method in question, selected compounds, or herbicidal compositions comprising them, can advantageously also be employed in a further number of crop plants for eliminating undesired plants. Examples of suitable crops are:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.

In addition, the selected compounds can also be used in crops which tolerate the action of herbicides owing to breeding, including recombinant methods. The generation of such crops is described hereinbelow.

The invention furthermore relates to a method of preparing a herbicidal composition, which comprises formulating selected compounds with suitable adjuvants to give crop protection products.

The present invention likewise relates to a method of preparing a growth-regulating composition, which comprises formulating selected compounds with suitable adjuvants to give crop protection products.

In this case the selected compounds can be formulated for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended use and the nature of the selected compounds; in any case, they should guarantee the finest possible distribution of the selected compounds. The herbicidal compositions comprise a herbicidally active amount of at least one selected compound and auxiliaries conventionally used in the formulation of herbicidal compositions.

For the preparation of emulsions, pastes or aqueous or oily formulations and dispersible concentrates (DC), the selected compounds can be dissolved or dispersed in an oil or solvent, it being possible to add further formulation auxiliaries for homogenization purposes. However, it is also possible to prepare liquid or solid concentrates from selected compound, if appropriate solvents or oil and, optionally, further auxiliaries comprising liquid or solid concentrates, and these concentrates are suitable for dilution with water. The following can be mentioned: emulsifiable concentrates (EC, EW), suspensions (SC), soluble concentrates (SL), dispersible concentrates (DC), pastes, pills, wettable powders or granules, it being possible for the solid formulations either to be soluble or dispersible (wettable) in water. In addition, suitable powders or granules or tablets can additionally be provided with a solid coating which prevents abrasion or premature release of the active ingredient.

In principle, the term "auxiliaries" is understood as meaning the following classes of compounds: antifoam agents, thickeners, wetters, stickers, dispersants, emulsifiers, bactericides and/or thixotropic agents. The skilled worker is familiar with the meaning of the abovementioned agents.

SLs, EWs and ECs can be prepared by simply mixing the constituents in question; powders can be prepared by mixing or grinding in specific types of mills (for example hammer mills). DCs, SCs and SEs are usually prepared by wet milling, it being possible to prepare an SE from an SC by addition of an organic phase which may comprise further auxiliaries or selected compounds. The preparation is known. Powders, materials for spreading and dusts can advantageously be prepared by mixing or concomitantly grinding the active substances together with a solid carrier. Granules, for example coated granules, impregnated granules and homogeneous granules, can be prepared by binding the selected compounds to solid carriers. The skilled worker is familiar with further details regarding their preparation, which are mentioned for example in the following publications: U.S. Pat. No. 3,060,084, EP-A 707445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley V C H Verlag GmbH, Weinheim (Federal Republic of Germany), 2001.

The skilled worker is familiar with a multiplicity of inert liquid and/or solid carriers which are suitable for the formulations according to the invention, such as, for example, liquid additives such as mineral oil fractions of medium to high boiling point such as kerosene or diesel oil, furthermore coal tar oils and oils of vegetable or animal origin, aliphatic, cyclic and aromatic hydrocarbons, for example paraffin, tetrahydrophthalene, alkylated naphthalenes or their derivatives, alkylated benzenes or their derivatives, alcohols such as methanol, ethanol, propanol, butanol and cyclohexanol, ketones such as cyclohexanone, or strongly polar solvents, for example amines such as N-methylpyrrolidone or water.

Examples of solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The skilled worker is familiar with the multiplicity of surface-active substances (surfactants) which are suitable for the formulations according to the invention such as, for example, alkali metal salts, alkaline earth metal salts or ammonium salts of aromatic sulfonic acids for example lignosulfonic acid, phenol sulfonic acid, naphthalenesulfonic acid, and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated caster oil, polyoxyethylene alkyl ethers or polyoxypropylene alkyl ethers, lauryl alcohol polyglycol ether acetate, sorbitol esters, lignin-sulfite waste liquors or methylcellulose.

The herbicidal compositions, or the selected compounds, can be applied pre- or post-emergence. If the selected compounds are less well tolerated by certain crop plants, application techniques may be used in which the selected compounds are spread, with the aid of the spraying apparatus, in such a way that they come into as little contact, if any, with the leaves of the sensitive crop plants while the selected compounds reach the leaves of undesired plants which grow underneath, or the bare soil surface (post-directed, lay-by).

Depending on the intended aim, the season, the target plants and the growth stage, the application rates of selected compounds amount to 0.001 to 3.0, preferably 0.01 to 1.0 kg/ha.

The invention is illustrated in greater detail by the examples which follow, which are not to be considered as limiting.

Providing the herbicidal target furthermore enables a method for identifying a protein with the biological activity of an SHMT which is not inhibited, or inhibited to a limited extent only, by a herbicide which has SHMT as its site of action, for example the herbicidally active selected compounds. In the following text, such a protein which differs in this way from SHMT is referred to as SHMT variant. Analogously to what has been said above, the term SHMT again preferably refers to mitochondrial SHMT.

In a preferred embodiment, the abovementioned method for generating variants of nucleic acid sequences comprising
i. a nucleic acid sequence with the nucleic acid sequence shown in SEQ ID NO:7; or
ii. a nucleic acid sequence which, on the basis of the degeneracy of the genetic code, can be derived from the amino acid sequence shown in SEQ ID NO:8 by back translation; or iii. functional equivalents of the nucleic acid sequence SEQ ID NO:7 with at least 46%, 47%, 48%, 49%, 50%, 51%, 52%, 53%, 54%, 55%, 56%, 57%, 58%, 59%, with preference at least 60%, 61%, 62%, 63%, 64%, 65%, 66%, 67%, 68%, 69% and 70%, preferably at least 71%, 72%, 73%, 74%, 75%, especially preferably at least 76%, 77%, 78%, 79%, 80%, 81%, 82%, 83%, 84%, 85%, 86%, 87%, 88%, 89%, very especially preferably at least 90%, 91%, 92%, 93%, 94%, 95%, 96%, 97%, 98%, 99% identity to the SEQ ID NO:7 comprises the following steps:
a) expressing the proteins encoded by the abovementioned nucleic acids in a heterologous system or or in a cell-free system;
b) randomized or directed mutagenesis of the protein by modification of the nucleic acid;
c) measuring the interaction of the modified gene product with the herbicide;
d) identifying derivatives of the protein which show less interaction;
e) assaying the biological activity of the protein after application of the herbicide; and
f) selecting the nucleic acid sequences which have a modified biological activity against the herbicide.

The sequences selected by the above-described methods are advantageously introduced into an organism. The invention therefore furthermore relates to an organism prepared by this method. The organism is preferably a plant, especially preferably one of the above-defined crop plants, very especially preferably potato, tobacco, linseed, oilseed rape, soya, barley, maize, cotton, wheat, pineapple, pawpaw or pea.

Thereafter, intact plants are regenerated and the resistance to the selected compound is checked in intact plants.

Modified proteins and/or nucleic acids which are capable of conferring, in plants, resistance to the selected compounds can also be prepared from the abovementioned nucleic acid sequences via what is known as site-directed mutagenesis; by means of this mutagenesis, for example the stability and/or activity of the target protein or the characteristics such as binding of the abovementioned inhibitors according to the invention can be improved or modified in a highly specific manner.

For example, Zhu et al. (Nature Biotech., Vol. 18, May 2000: 555-558) have described a site-directed mutagenesis method in plants which can be used advantageously.

Moreover, modifications can be achieved via the PCR method described by Spee et al. (Nucleic Acids Research, Vol. 21, No. 3, 1993: 777-78) using dITP for the random mutagenesis, or by the further-improved method of Rellos et al. (Protein Expr. Purif., 5, 1994: 270-277).

A further possibility of producing these modified proteins and/or nucleic acids is an in-vitro recombination technique for molecular evolution which has been described by Stemmer et al. (Proc. Natl. Acad. Sci. USA, Vol. 91, 1994: 10747-10751), or the combination of the PCR and recombination method described by Moore et al. (Nature Biotechnology Vol. 14, 1996: 458-467).

A further way for the mutagenesis of proteins is described by Greener et al. in Methods in Molecular Biology (Vol. 57, 1996: 375-385). A method for modifying proteins using the microorganism E. coli XL-1 Red is described in EP-A-0 909 821. During its replication, this microorganism generates mutations in the nucleic acids which have been introduced and thus leads to a modification of the genetic information.

Advantageous nucleic acids and the proteins encoded by them can be identified readily by isolating the modified nucleic acids or the modified proteins and carrying out resistance tests. The former can then be introduced into plants, where they are capable of manifesting the resistance and thus lead to resistance to the herbicides.

Further methods of mutagenesis and selection are, for example, methods such as the in-vivo mutagenesis of seeds or pollen and the selection of resistant alleles in the presence of the inhibitors according to the invention, followed by genetic and molecular identification of the modified, resistant allele; so are the mutagenesis and selection of resistances in cell culture by propagating the culture in the presence of successively increasing concentrations of the inhibitors according to the invention. In this context, the increase of the spontaneous mutation rate by chemical/physical mutagenic treatment may be exploited. As described above, modified genes can also be isolated using microorganisms which have an endogenous or recombinant activity of the proteins encoded by the nucleic acids used in the method according to the invention, and which are sensitive to the inhibitors identified in accordance with the invention. Growing the microorganisms on media with increasing concentrations of inhibitors according to the invention permits the selection and evolution of resistant variants of the targets according to the invention. The mutation frequency, in turn, can be increased by mutagenic treatments.

Methods for the specific modification of nucleic acids are furthermore available (Zhu et al. Proc. Natl. Acad. Sci. USA, Vol. 96, 8768-8773 and Beethem et al., Proc. Natl. Acad. Sci. USA, Vol. 96, 8774-8778). These methods make possible the replacement, in the proteins, of those amino acids which are important for the binding of inhibitors by functionally analogous amino acids which, however, prevent the inhibitor from binding.

The invention furthermore therefore relates to a method for establishing nucleotide sequences which encode gene products which have a modified biological activity, the biological activity having been modified in such a way that an increased activity is present. An increased activity is understood as meaning an activity which is increased by at least 10%, preferably by at least 30%, especially preferably by at least 50%, very especially preferably by at least 100% in comparison with the starting organism, or the starting gene product.

Moreover, the biological activity can have been modified in such a way that the substances and/or compositions according to the invention no longer bind, or no longer properly bind, to the nucleic acid sequences and/or the gene products encoded by them. For the purposes of the invention, no longer, or no longer properly, is to be understood as meaning that the substances bind by at least 30% less, preferably at least 50% less, especially preferably by at least 70%, very especially preferably by at least 80%, or indeed no longer, to the modified nucleic acids and/or gene products in comparison with the starting gene product or the starting nucleic acids.

Yet a further aspect of the invention therefore relates to a transgenic plant which has been modified by the above-described method according to the invention.

Genetically modified transgenic plants which are resistant to substances found in accordance with the methods according to the invention and/or to compositions comprising these substances can also be generated by overexpressing the nucleic acid sequences used in the abovementioned methods according to the invention for identifying herbicides. The invention therefore furthermore relates to a method for the generation of transgenic plants which are resistant to substances found by a method according to the invention, which comprises overexpressing, in these plants, nucleic acids comprising
a) a nucleic acid sequence with the nucleic acid sequence shown in SEQ ID NO:7; or
b) a nucleic acid sequence which, on the basis of the degeneracy of the genetic code, can be derived from the amino acid sequence shown in SEQ ID NO:8 by back translation; or
c) functional equivalents of the nucleic acid sequence SEQ ID NO:7 with at least 46%, 47%, 48%, 49%, 50%, 51%, 52%, 53%, 54%, 55%, 56%, 57%, 58%, 59%, with preference at least 60%, 61%, 62%, 63%, 64%, 65%, 66%, 67%, 68%, 69% and 70%, preferably at least 71%, 72%, 73%, 74%, 75%, especially preferably at least 76%, 77%, 78%, 79%, 80%, 81%, 82%, 83%, 84%, 85%, 86%, 87%, 88%, 89%, very especially preferably at least 90%, 91%, 92%, 93%, 94%, 95%, 96%, 97%, 98%, 99% identity to the SEQ ID NO:7.

A similar method is described by way of example in Lermantova et al., Plant Physiol., 122, 2000: 75-83.

The above-described methods according to the invention for generating resistant plants make possible the development of novel herbicides which have as complete as possible an action which is independent of the plant species (what are known as nonselective herbicides), in combination with the development of useful plants which are resistant to the nonselective herbicide. Useful plants which are resistant to nonselective herbicides have already been described on several occasions. In this context, one can distinguish between several principles for achieving a resistance:
a) Generation of resistance in a plant via mutation methods or recombinant methods by markedly overproducing the protein which acts as target for the herbicide and by the fact that, owing to the large excess of the protein which acts as target for the herbicide, the function exerted by this protein in the cell is even retained after application of the herbicide.
b) Modification of the plant such that a modified version of the protein which acts as target of the herbicide is introduced and that the function of the newly introduced modified protein is not adversely affected by the herbicide.
c) Modification of the plant such that a novel protein/a novel RNA is introduced wherein the chemical structure of the protein or of the nucleic acid, such as of the RNA or the DNA, which structure is responsible for the herbicidal action of the low-molecular-weight substance, is modified so that, owing to the modified structure, a herbicidal action can no longer be developed, that is to say that the interaction of the herbicide with the target can no longer take place.
d) The function of the target is replaced by a novel gene introduced into the plant, creating what is known as an alternative pathway.
e) The function of the target is taken over by another gene which is present in the plant, or by its gene product.

The present invention therefore furthermore comprises the use of plants, genes affected by T-DNA insertion which have the abovementioned nucleic acid sequences SEQ ID NO:7 and their functional equivalents for the development of novel herbicides. The skilled worker is familiar with alternative methods of identifying homologous nucleic acids, for example in other plants with similar sequences, such as, for example, using transposons. The present invention therefore also relates to the use of alternative insertion mutagenesis methods for inserting foreign nucleic acid into the nucleic acid sequences SEQ ID NO:7, into sequences derived from these sequences on the basis of the genetic code and/or their derivatives in other plants.

The transgenic plants are generated using one of the above-described use forms of the expression cassettes according to the invention by customary transformation methods which are likewise described above.

The expression efficacy of the recombinantly expressed SHMT can be determined for example in vitro by shoot-meristem propagation or by a germination test. Moreover, an expression of the SHMT gene, which has been modified in terms of nature and level, and its effect on the resistance to SHMT inhibitors in test plants can be tested in greenhouse experiments.

General DNA Manipulation and Cloning Methods

Cloning methods such as, for example, restriction cleavages, agarose gel electrophoreses, purification of DNA fragments, transfer of nucleic acids to nitrocellulose and nylon membranes, linking DNA fragments, transformation of *Escherichia coli* cells, growing bacterium and sequence analyses of recombinant DNA were carried out as described by Sambrook et al. (1989) (Cold Spring Harbor Laboratory Press: ISBN 0-87969-309-6) and Ausubel, F. M. et al., Current Protocols in Molecular Biology, Greene Publishing Assoc. and Wiley-Interscience (1994); ISBN 0-87969-309-6.

Molecular-biological standard methods for plants and plant transformation methods are described in Schultz et al., Plant Molecular Biology Manual, Kluwer Academic Publishers (1998), Reither et al., Methods in *Arabidopsis* Research, World scientific press (1992) and *Arabidopsis*: A Laboratory Manual (2001), ISBN 0-87969-573-0.

The bacterial strains used hereinbelow (*E. coli* DH5α, XL-1 blue, BL21DE(3)) were obtained from Stratagene, BRL Gibco or Invitrogen, Carlsberg, Calif. The vectors used for cloning were pCR T7CT TOPO, pCR T7/NT TOPO and pCR 2.1 TOPO from Invitrogen and pUC 19 from Amersham Pharmacia (Freiburg) and the vector pBinAR (Höfgen and Willmitzer, Plant Science 66, 1990, 221-230).

EXAMPLE 1

Generation of a cDNA Library in the Plant Transformation Vector

To generate a cDNA library (hereinbelow termed "binary cDNA library") in a vector which can be used directly for transforming plants, mRNA was isolated from a variety of plant tissues and transcribed into double-stranded cDNA using the cDNA Synthese Kit (Amersham Pharmacia Biotech, Freiburg). The cDNA first-strand synthesis was carried out using $T_{12-18}$ oligonucleotides following the manufacturer's instructions. After size fractionation and the ligation of EcoRI-NotI adapters following the manufacturer's instructions and filling up the overhangs with Pfu DNA polymerase (Stratagene), the cDNA population was normalized. The method of Kohci et al, 1995, Plant Journal 8, 771-776 was followed, the cDNA being amplified by PCR with the oligonucleotide N1 under the conditions given in Table 1.

TABLE 1

| Temperature [° C.] | Time [sec] | Number of cycles |
|---|---|---|
| 94 | 300 | 1 |
| 94 | 8 | 10 |
| 52 | 60 | |
| 72 | 180 | |
| 94 | 8 | 10 |
| 50 | 60 | |
| 72 | 180 | |
| 94 | 8 | 10 |
| 48 | 60 | |
| 72 | 180 | |
| 72 | 420 | 1 |

The resulting PCR product was bound to the column matrix of the PCR purification kit (Qiagen, Hilden) and eluted with 300 mM NaP buffer, pH 7.0, 0.5 mM EDTA, 0.04% SDS. The DNA was denatured for 5 minutes in a boiling water bath and subsequently renatured for 24 hours at 60° C. 50 µl of the DNA were applied to a hydroxylapatite column and the column was washed 3 times with 1 ml of 10 mM NaP buffer, pH 6.8. The bound single-stranded DNA was eluted with 130 mM NaP buffer, pH 6.8, precipitated with ethanol and dissolved in 40 µl of water. 20 µl of growth were used for a further PCR amplification as described above. After further ssDNA concentration, a third PCR amplification was carried out as described above.

The plant transformation vector for taking up the cDNA population which had been generated as described above was generated via restriction enzyme cleavage of the vector pUC18 with SbfI and BamHI, purification of the vector fragment followed by filling up the overhangs with Pfu DNA polymerase and relegation with T4 DNA ligase (Stratagene). The resulting construct is hereinbelow termed pUC18SbfI-.

The vector pBinAR was first cleaved with NotI, the ends were filled up and the vector was relegated, cleaved with SbfI, the ends were filled up and the vector was relegated and subsequently cleaved with EcoRI and HindIII. The resulting fragment was ligated into a derivative of the binary plant transformation vector pPZP (Hajdukiewicz, P, Svab, Z, Maliga, P., (1994) Plant Mol Biol 25: 989-994) which makes possible the transformation of plants by means of *agrobacterium* and mediates kanamycin resistance in transgenic plants. The construct generated thus is hereinbelow termed pSun12/35S.

pUC18SbfI—was used as template in a polymerase chain reaction (PCR) with the oligonucleotides V1 and V2 (see Table 2) and Pfu DNA polymerase. The resulting fragment was ligated into the SmaI-cut pSun12/35S, giving rise to pSunblues2. Following cleavage with NotI, dephosphorylation with shrimp alkaline phosphatase (Roche Diagnostics, Mannheim) and purification of the vector fragment, pSunblues2 was ligated with the normalized, likewise NotI-cut cDNA population. Following transformation into *E. coli* Xl-1blue (Stratagene), the resulting clones were deposited into microtiter plates. The binary cDNA library comprises cDNAs in "sense"- and in "antisense" orientation under the control of the cauliflower mosaic virus 35S promoter, and, after transformation into tobacco plants, these cDNAs can, accordingly, lead to "cosuppression" and "antisense" effects.

TABLE 2

Oligonucleotides used

| Oligonucleotide | Nucleic acid sequence |
|---|---|
| N1 | 5'-AGAATTCGCGGCCGCT-3'<br>[SEQ ID NO: 9] |
| V1 (PWL93not) | 5'-CTCATGCGGCCGCGCGCAACGCAATTAATGTG-3'<br>[SEQ ID NO: 10] |
| V2 (pWL92) | 5'-TCATGCGGCCGCGAGATCCAGTTCGATGTAAC-3'<br>[SEQ ID NO: 11] |
| G1 (35S) | 5'-GTGGATTGATGTGATATCTCC-3'<br>[SEQ ID NO: 12] |
| G2 (OCS) | 5'-GTAAGGATCTGAGCTACACAT-3'<br>[SEQ ID NO: 13] |

EXAMPLE 2

Transformation and Analysis of Tobacco Plants

Selected clones of the binary cDNA library were transformed into *Agrobacterium tumefaciens* C58C1:pGV2260 and (Deblaere et al., Nucl. Acids. Res. 13(1984), 4777-4788) and incubated with Streptomycin/Spectinomycin selection. The material used for the transformation of tobacco plants (*Nicotiana tabacum* cv. Samsun NN) with the binary clones nt002001035r and nt002001036r was an overnight culture of a positively transformed agrobacterial colony diluted with YEB medium to OD600=0.8-1.6. Leaf discs of sterile plants (approx. 1 cm² each) were incubated for 5-10 minutes with a 1:50 agrobacterial dilution in a Petri dish. This was followed by incubation in the dark for 2 days at 25° C. on Murashige-Skoog medium (Physiol. Plant. 15(1962), 473) supplemented with 2% sucrose (2MS medium) and 0.8% Bacto agar. The cultivation was continued after 2 days at a 16-hour-light/8-hour-darkness photoperiod and continued in a weekly rhythm on MS medium supplemented with 500 mg/l Claforan (cefotaxime sodium), 50 mg/l kanamycin, 1 mg/l benzylaminopurin (BAP), 0.2 mg/l naphthylacetic acid and 1.6 g/l glucose. Regenerated shoots were transferred onto an MS medium supplemented with kanamycin and Claforan. Transgenic plants of line P__0000000315 were generated in this manner.

The integration of the clone cDNA into the genome of the transgenic lines was detected via PCR with the oligonucleotides G1 and G2 (see Table 2) and genomic DNA prepared from the transgenic lines in question. To this end, TAKARA Taq DNA polymerase was preferably employed for this purpose, following the manufacturer's instructions (MoBiTec, Göttingen). The cDNA clone of the binary cDNA library, which clone had been used for the transformation, acted as template for a PCR reaction as the positive control. PCR products with an identical size or, if appropriate, identical cleavage patterns which were obtained after cleavage with a variety of restriction enzymes acted as proof that the corresponding cDNA had been integrated. In this manner, the insert of clone nt002001035r was detected in the transgenic plants with the abovementioned phenotypes. Furthermore, the repression of an approx. 1.7 kb mRNA hybridized under stringent conditions with the cDNA of clone nt002001035r was detected in leaf tissues of the transgenic plants in comparison with control plants (*Nicotiana tabaccum*, Varietät Samsun NN). To this end, a probe of the nt002001035r insert was labeled with the aid of the High-prime DNA labeling kit (Roche, Mannheim). The probe was used for the hybridization of total RNA or mRNA from tissues of the relevant transgenic plant and control plants, which RNA had been separated by standard methods and transferred to nitrocellulose membranes (Schleicher and Schüll, Dassel, Germany).

After the shoots had been transferred into soil, the plants were observed for 2-20 weeks in the greenhouse for the manifestation of phenotypes. It emerged that transgenic plants of line P_0000000315 were similar in phenotype. Four plants of line P_0000000315 (18/8, 18/32, 18/75 and 18/77), which had the nt002001035r insert, showed pronounced growth retardation after 2 weeks and also chlorotic leaves and, in some cases, necroses. Moreover, line 18/75 produced virtually no roots and was eventually damaged to such a degree that it died after approximately 6 weeks.

EXAMPLE 3

Sequence Analysis of the Clones

Part of the chimeric cDNA of clone nt002001035r (SEQ ID NO:1) of cDNA (Nucleotide 506-652) encodes a peptide fragment (SEQ ID NO:2) with a high degree of identity to plant SHMTs. Sequence alignments with the aid of the BLAST algorithm (Altschul et al. 1990, J. Mol. Biol. 215, pp. 403-410) with a tobacco EST database revealed further clones with >99% identity to the part-region of the SEQ ID NO:1 and with a high degree of identity to mitochondrial SHMTS. One of these clones (clone nt006100023, SEQ ID NO:3) was sequenced and is chimeric. The part-region of SEQ ID NO:3 which encodes a mitochondrial SHMT peptide of 180 amino acids (SEQ ID NO:2) comprises the 378 bp region of SEQ ID NO:1 which encodes a mitochondrial SHMT peptide fragment. A further nonchimeric clone (clone nt 006043063, SEQ ID NO:5), which is identical with the SHMT-encoding part-region of SEQ ID:01 with the exception of nucleotide positions 11, 262 and 333 was also transformed in tobacco plants. The phenotypes of the resulting transgenic plants were identical to those of the plants of line P_0000000315.

Thus, it was shown for the first time and in a surprising manner that the natural expression of SHMT-encoding sequences is essential for plants and that reduced expression leads to damage as can be seen on the phenotypes mentioned in Example 2. The suitability of SHMT as target for herbicides was thus demonstrated.

Based on the sequence of nt006043063r, a 5'-RACE was carried out with tobacco cDNA, following the manufacturer's instructions (SMART-Kit, Clontech). The sequence of the full-length SHMT cDNA obtained in this manner was determined (SEQ ID NO: 7). With the exception of one nucleotide (position 81), the sequence is identical to SEQ ID NO:5 in the overlap region (from nucleotide 1288 to 1760). SEQ ID NO: 7 is 1835 nt in length and comprises an open reading frame of 1554 bp which encodes a polypeptide 518 amino acids in length (from nucleotide 56 to 1609, SEQ ID NO: 8). The highest degree of identity is found between SEQ ID NO: 7 and a potato mitochondrial SHMT (86.8% identity with Genbank No. Z25863).

EXAMPLE 4

Expression in E. coli

An *Arabidopsis* cDNA encoding a mitochondrial SHMT (SHM1, Genbank Accession Number: AJ271726) was overexpressed in E. coli bacteria in order to generate active protein with a plant SHMT activity.

To this end, the coding region of AJ271726 was amplified from cDNA libraries by PCR and ligated into the vector pCR 2.1 TOPO by standard techniques (constructs SHMT1 and SHMT2, Table 8). The resulting constructs were subsequently amplified by PCR by means of specific oligonucleotides, and resulting fragments were ligated into the expression vectors pCR T7/CT TOPO and pCR T7/NT-TOPO (Invitrogen) (constructs SHMT 3-6, Table 7). In this manner, fusion proteins with C-terminal or N-terminal hexahistidine tags were generated. The use of the oligonucleotides shown in Table 8 in the cloning step gave N-terminally truncated versions of SHMT in order to exclude the mitochondrial transit sequence which might counteract functional expression. Since the mitochondrial transit sequence of SHMT is not definitely known, a variety of N-terminally truncated versions were generated. In order to delimit the region to be deleted, it was possible to refer to the literature (Turner et al. JBC 19, pp. 13528-13534, 1992). The PCR was carried out in 36 cycles following standard conditions (for example as described by Sambrook, J. et al. (1989) "Molecular cloning: A laboratory manual", Cold Spring Harbor Laboratory Press), the annealing temperatures being between 45 and 55° C. and the polymerization time being in each case 60 seconds per 1000 bp. The templates and the primers used for the template in question are shown in Table 7 together with the annealing temperatures.

TABLE 7

| Construct | Annealing temperature [° C.] | Primer (Nucleic acid sequence) |
|---|---|---|
| SHMT1 * 1 | 60 | 5'-AAATGGCGATGGCCATGGC-3' [SEQ ID NO: 14] |
| | | 5'-TGGGGTGAAACAGTTTAGTTC-3' [SEQ ID NO: 15] |
| SHMT2 * 1 | 58 | 5'-AAACCAGAGATAGAGAGAGG-3' [SEQ ID NO: 16] |
| | | 5'-ACATGTATCATCTATACATTCC-3' [SEQ ID NO: 17] |
| SHMT3 ** 2 | 60 | 5'-ATGGCGATGGCCATGGCT-3' [SEQ ID NO: 18] |
| | | 5'-TGGGGTGAAACAGTTTAGTTC-3' [SEQ ID NO: 19] |
| SHMT4 ** 2 | 60 | 5'-ATGAAGGAAAGATCTCGTGTC-3' [SEQ ID NO: 20] |
| | | 5'-TGGGGTGAAACAGTTTAGTTC-3' [SEQ ID NO: 21] |
| SHMT5 ** 2 | 55 | 5'-ATGTCTTTGCCCAGTGAAG-3' [SEQ ID NO: 22] |
| | | 5'-TGGGGTGAAACAGTTTAGTTC-3' [SEQ ID NO: 23] |

TABLE 7-continued

| Construct | Annealing temperature [° C.] | Primer (Nucleic acid sequence) |
|---|---|---|
| SHMT6 *** 2 | 60 | 5'-ATGAAGGAAAGATCTCGTGTC-3' [SEQ ID NO: 24] |
| | | 5'-TGGGGTGAAACAGTTTAGTTC-3' [SEQ ID NO: 25] |
| SHMT7 *** 2 | 55 | 5'-ATGGCGATGGCCATGGCT-3' [SEQ ID NO: 26] |
| | | 5'-TGGGGTGAAACAGTTTAGTTC-3' [SEQ ID NO: 27] |

* Vector used: pCR 2.1 TOPO
** Vector used: pCR T7/CT-TOPO
*** Vector used: pCR T7/NT-TOPO
1 Template: *Arabidopsis thaliana* cDNA library
2 Template: SHMT1

The PCR products were ligated into the vectors shown in Table 7 and transformed into *E. coli*. Expression was performed in *E. coli* BL21(DE3) strains such as BL21(DE3) pLysS or BL21(DE3)pLysE (Invitrogen), BL21-CodonPlus (DE3) or BL21-CodonPlus(DE3)RIL (Stratagene) following induction with IPTG. Standard protocols (Invitrogen) were followed.

The expression products of SHMT6 and SHMT7 were purified by affinity chromatography on Ni-agarose. The manufacturer's instructions were followed (Qiagen).

EXAMPLE 5

In Vitro Assay Systems

SHMT can be isolated from plant mitochondria as described and determined by means of a radioactive method according to the invention (Bourguignon et al. Biochem. J. 255, pp. 169-178, 1988). The activity of the SHMT protein which had been expressed recombinantly in Example 4 and, if appropriate, purified was also determined using this method according to the invention.

As an alternative, the SHMT reaction was assayed by means of an HPLC-aided separation method which is based on the separation of tetrahydrofolate and C1-tetrahydrofolate. In this method, the enzyme-comprising aqueous assay solution (0.4 5 mM 2-mercaptoethanol, 2 mM tetrahydrofolate, 20 mM serine, 56 mM $KH_2PO_4$ pH 7.4), which compriseed 1-100% g of mitochondrial SHMT, was incubated for 30 minutes with shaking, denatured with 0.1 ml of 0.36M HCl per 100 ml or assay solution and freed from precipitates by spinning for 5 minutes at a high g number (10000 g).

The HPLC runs were carried out with a Symmetry C18 column (3.5 µM 4.6×10 mm; sample temperature 10° C., column temperature 25° C.; flow rate: 1 ml/min; $\lambda$=288 nm), the column being washed for 0.5 minute with 95% buffer A (5% by volume acetonitrile in water) after application of the sample. The analytical separation was carried out by applying a gradient of 0-100% buffer B (water) over a period of 6 minutes. Moreover, the enzymatic activity was determined analogously to the method described by Stover and Schirch (Anal. Biochem. 202, pp. 82-88). This method according to the invention is based on coupling the SHMT reaction with the reaction catalyzed by NAD-dependent methylenetetrahydrofolate dehydrogenase (MTD) and photometric measurement at 340 nm. The amounts of the auxiliary enzyme MTD which are required for this purpose were obtained by a recombinant expression of *Sacoharomyces cerevisiae* MTD in *E. coli* as follows: following isolation of the MTD-encoding nucleic acid fragment from genomic DNA as described by Appling and West (Methods in Enzymology 281, pp. 178-188), it was cloned into the vector pCR 2.1 TOPO. The resulting construct was amplified via PCR using the oligonucleotides 5'-TTTTTCTTTAGACAGTTC-TACGTTC-3' and 5'-ATGTCGAAGCCTGGTCGTA-3'. The PCR was carried out in 36 cycles under standard conditions (for example those described by Sambrook, J. et al. (1989) "Molecular cloning: A laboratory manual", Cold Spring Harbor Laboratory Press), the annealing temperature being 55° C. and the polymerization time being in each case 60 seconds per 1000 bp. The PCR products were ligated into the expression vector pCR T7/CT-TOPO (construct MTD) and expressed in *E. coli* BL21 (DE3) strains such as BL21 (DE3)pLysS or BL21 (DE3)pLysE (Invitrogen), BL21-CodonPlus(DE3) or BL21-CodonPlus(DE3)RIL (Stratagene). Standard protocols (Invitrogen) were followed. The expression product of the construct MTD was purified by affinity chromatography on Ni-agarose as specified by the manufacturer (Qiagen).

We claim:

1. A method for identifying herbicidally active substances comprising
   a) bringing a polypeptide with the enzymatic activity of a serine hydroxymethyltransferase into contact with one or more test compounds under conditions which permit the test compound(s) to bind to the polypeptide; and
   b) detecting whether the test compound inhibits the activity of the polypeptide of a), wherein inhibition is an indication that the test compound is herbicidally active, wherein said polypeptide is encoded by a nucleic acid sequence selected from the group consisting of:
   a) the nucleic acid sequence shown in SEQ ID NO:7;
   b) a nucleic acid sequence encoding the amino acid sequence shown in SEQ ID NO:8; and
   c) a nucleic acid sequence encoding serine hydroxymethyltransferase having at least 95% identity to SEQ ID NO:7.

2. The method according to claim 1, wherein said polypeptide with the enzymatic activity of a serine hydroxymethyltransferase is necessary for survival and growth of a plant.

3. The method as claimed in claim 1, wherein the substances are identified in a high-throughput screening.

4. The method according to claim 1, wherein said serine hydroxymethyltransferase has the sequence according to SEQ ID NO:8.

5. The method according to claim 1, wherein said serine hydroxymethyltransferase is mitochondrial serine hydroxymethyltransferase.

6. The method according to claim 1, wherein said serine hydroxymethyltransferase is obtainable from *Nicotiana tabacum*.

7. A method for identifying herbicidally active substances, comprising
   a) culturing an organism that expresses a plant serine hydroxymethyltransferase which is encoded by a nucleic acid sequence selected from the group consisting of:
      i) the nucleic acid sequence sequence shown in SEQ ID NO: 7;
      ii) a nucleic acid sequence encoding the amino acid sequence as shown in SEQ ID NO:8; and
      iii) a nucleic acid sequence encoding serine hydroxymethyltransferase having at least 95% identity to SEQ ID NO:7;
   b) preparing a cell digest of the organism and bringing the serine hydroxymethyltransferase in the cell digest, in partially or homogeneously purified form, into contact with a test compound; and
   c) determining whether the test compound inhibits the activity of the serine hydroxymethyltransferase, where the activity of the serine hydroxymethyltransferase incubated with the test compound is compared with the activity of a serine hydroxymethyltransferase which is not incubated with a test compound; wherein inhibition is an indication that the test compound is herbicidally active.

8. The method according to claim 7, wherein, in step c), the activity of the serine hydroxymethyltransferase is determined by the chromatographic isolation and quantification of tetrahydrofolate and C1-tetrahydrofolate.

* * * * *